(12) United States Patent
Lange et al.

(10) Patent No.: US 8,410,135 B2
(45) Date of Patent: Apr. 2, 2013

(54) 4,5 DIHYDRO-(1H)-PYRAZOLE DERIVATIVES AS CANNABINOID $CB_1$ RECEPTOR MODULATORS

(75) Inventors: Josephus H. M. Lange, Weesp (NL); Hendrik C. Wals, Weesp (NL); Bernard J. Van Vliet, Weesp (NL); Mahmut Yildirim, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 644 days.

(21) Appl. No.: 12/136,986

(22) Filed: Jun. 11, 2008

(65) Prior Publication Data

US 2008/0312276 A1 Dec. 18, 2008

Related U.S. Application Data

(60) Provisional application No. 60/944,194, filed on Jun. 15, 2007.

(51) Int. Cl.
| | | |
|---|---|---|
| C07D 231/12 | (2006.01) | |
| C07D 403/04 | (2006.01) | |
| A61K 31/4152 | (2006.01) | |
| A61K 31/4155 | (2006.01) | |
| A61P 9/10 | (2006.01) | |
| A61P 19/10 | (2006.01) | |
| A61P 25/04 | (2006.01) | |
| A61P 25/08 | (2006.01) | |
| A61P 25/28 | (2006.01) | |
| A61P 1/00 | (2006.01) | |

(52) U.S. Cl. ..... 514/313; 514/403; 546/162; 548/364.4; 548/379.1; 548/379.4

(58) Field of Classification Search ............... 548/379.1, 548/379.4
See application file for complete search history.

(56) References Cited

U.S. PATENT DOCUMENTS

| | | | | |
|---|---|---|---|---|
| 3,772,328 | A | * 11/1973 | Stapfer et al. | 548/564 |
| 3,780,058 | A | * 12/1973 | Brzozowski et al. | 548/379.4 |
| 4,996,327 | A | * 2/1991 | Merkle et al. | 548/373.1 |
| 5,068,241 | A | * 11/1991 | Fuchs et al. | 514/403 |
| 6,974,810 | B2 | * 12/2005 | Lange et al. | 514/236.5 |
| 7,528,162 | B2 | * 5/2009 | Kruse et al. | 514/403 |
| 7,608,718 | B2 | * 10/2009 | Lange et al. | 546/211 |

FOREIGN PATENT DOCUMENTS

| | | | |
|---|---|---|---|
| EP | 467614 | * | 1/1992 |
| WO | WO 03/026647 A1 | | 4/2003 |
| WO | WO 03/026648 A1 | | 4/2003 |
| WO | WO 2005/074920 A1 | | 8/2005 |

OTHER PUBLICATIONS

Internal Search Report and Written Opinion for International Application No. PCT/EP2008/057367, filed Jun. 12, 2008, mailed Mar. 25, 2009 (12 pages).

* cited by examiner

*Primary Examiner* — Fiona T Powers
(74) *Attorney, Agent, or Firm* — Finnegan, Henderson, Farabow, Garrett & Dunner LLP

(57) ABSTRACT

The invention is directed to 4,5-dihydro-(1H)-pyrazole (pyrazoline) derivatives as cannabinoid $CB_1$ receptor modulators, to pharmaceutical compositions comprising these compounds, to methods for their syntheses, to methods for preparing novel intermediates useful for their syntheses, and to methods for preparing compositions. The invention also relates to the uses of compounds and compositions administered to patients to achieve a therapeutic effect in multiple sclerosis, traumatic brain injury, pain including chronic pain, neuropathic pain, acute pain and inflammatory pain, osteoporosis, appetite disorders, epilepsy, Alzheimer's disease, Tourette's syndrome, cerebral ischaemia, emesis, nausea, and gastrointestinal disorders.

Compounds of the present disclosure are directed to formula (I):

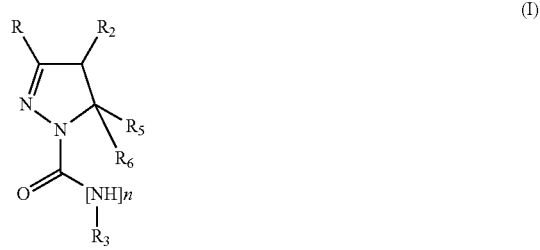

wherein the substituents have the definitions given in the specification.

14 Claims, No Drawings

4,5 DIHYDRO-(1H)-PYRAZOLE DERIVATIVES AS CANNABINOID CB₁ RECEPTOR MODULATORS

This application claims the benefit of U.S. provisional application No. 60/944,194, filed Jun. 15, 2007, the disclosure of which is incorporated herein by reference.

The present disclosure relates to the fields of pharmaceutical and organic chemistry, and provides 4,5-dihydro-(1H)-pyrazole (pyrazoline) derivatives as cannabinoid $CB_1$ receptor modulators, intermediates for synthesizing these compounds, formulations comprising these compounds, methods for preparing these compounds, methods for preparing compositions comprising these compounds, and methods of treatment using these compounds.

Cannabinoid (CB) receptors are part of the endocannabinoid system which are involved in neurological-, psychiatric-, cardiovascular-, gastrointestinal-, reproductive- and eating disorders as well as in cancer (De Petrocellis, 2004; Di Marzo, 2004; Lambert, 2005; Vandevoorde, 2005).

$CB_2$ receptors occur predominantly in the immune system (spleen, tonsils, immune cells), but also in astrocytes, microglial cells, and to some extend in the central nervous system. $CB_2$ receptor modulation has been linked to the perception of inflammatory and neuropathic pain, as well as allergies, asthma, multiple sclerosis, osteoporosis and (neuro)inflammatory conditions (Van Sickle, 2005; Giblin, 2007; Ibrahim, 2005; Ashton, 2006, Ofek, 2006).

SR141716A, now known as rimonabant, and other $CB_1$ receptor modulators, including $CB_1/CB_2$ receptor subtype selective receptor antagonists, have several potential therapeutic applications including medicaments for treating psychosis, anxiety, depression, attention deficits, memory disorders, cognitive disorders, appetite disorders, obesity, addiction, appetence, drug dependence, neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, septic shock, glaucoma, diabetes, cancer, emesis, nausea, gastrointestinal disorders, gastric ulcers, diarrhea, sexual disorders, impulse control disorders and cardiovascular disorders (Boyd, 2005; Sorbera, 2005; Carai, 2005; Lange, 2004 & 2005; Hertzog, 2004; Smith, 2005; Thakur, 2005; Padgett, 2005; Muccioli, 2005 & 2006; Reggio, 2003; Adam, 2006; Hogenauer, 2007).

Diarylpyrazoline derivatives having cannabinoid $CB_1$ receptor antagonistic or inverse agonistic affinity have been claimed in WO 01/70700, WO 03/026647, WO 03/026648, WO 2005/074920, and were described by Lange (2004[a,b], 2005[a,b]). Pyrazoline derivatives which act as agonists or partial agonists on the $CB_1$ receptor have not been reported yet, but certain pyrazoline derivatives have been claimed as vermin controlling agents (JP 61 189270) and as mitotic kinesin inhibitors (WO2006/068933, WO2003079973).

Thus, there is a need to develop novel compounds with $CB_1$ receptor agonistic activity.

DESCRIPTION

Surprisingly, the inventors found that replacing the 3-aryl or 3-heteroaryl group in 4,5-dihydro-pyrazoles as described in WO 01/70700, with an optionally substituted alkyl moiety along with a different substitution pattern at the 1-position of the pyrazoline moiety and the presence of one or two alkyl substituents at the 5-position of the pyrazoline moiety results in novel compounds with potent $CB_1$ receptor affinity. Moreover, some of these compounds also showed affinity for $CB_2$ receptors, wherein these compounds may act as $CB_2$ receptor agonists, $CB_2$ receptor antagonists, or $CB_2$ receptor inverse agonists.

In one embodiment, the invention relates to compounds of formula (I):

or a tautomer, stereoisomer, N-oxide, isotopically-labelled analogue, or a
pharmacologically acceptable salt of any of the foregoing, wherein:

R is chosen from:
  $C_{3-10}$ linear alkyl, $C_{4-10}$ branched alkyl, $C_{4-10}$ alkynyl, $C_{3-10}$-heteroalkyl, and $C_{5-8}$-cycloalkyl-$C_{1-5}$-alkyl, which are optionally substituted with 1-3 fluorine atoms,
  aryl-$C_{1-3}$-alkyl and heteroaryl-$C_{1-3}$-alkyl, optionally substituted with 1-3 substituents Y, wherein Y is the same or different, and is chosen from methyl, ethyl, methoxy, ethoxy, halogen, trifluoromethyl, trifluoromethoxy and cyano,
  cyclopropyl, optionally substituted with $C_{1-5}$-alkyl, benzyl, aryl, and heteroaryl, which are optionally substituted with 1-3 substituents Y as defined above;
$R_2$ is chosen from aryl and heteroaryl, which are optionally substituted with 1-5 substituents Y as defined above;
n is 0 or 1;
$R_3$ is chosen from:
  linear and branched $C_{3-10}$ alkyl, $C_{3-8}$ cycloalkyl, $C_{5-10}$ bicycloalkyl, $C_{6-10}$ tricycloalkyl, and $C_{8-11}$ tetracycloalkyl, which are optionally substituted with 1-5 substituents chosen from methyl, ethyl, hydroxy, amino, and fluoro,
  $C_{3-8}$ cycloalkylsubstituted with aryl and heteroaryl, wherein the aryl and heteroaryl are optionally substituted with 1-5 substituents Y, wherein Y is the same or different, and is chosen from methyl, ethyl, methoxy, ethoxy, halogen, trifluoromethyl, trifluoromethoxy and cyano,
  $C_{5-8}$ heterocycloalkyl, $C_{6-10}$ bicycloheteroalkyl, and $C_{7-10}$ tricycloheteroalkyl, which are optionally substituted with 1-5 substituents chosen from methyl, ethyl, hydroxy, amino and fluoro,
  $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, which are optionally substituted with 1-5 substituents chosen from methyl, ethyl, hydroxy, amino and fluoro,
  branched and linear $C_{3-8}$ heterocycloalkyl-$C_{1-3}$-alkyl, $C_{5-10}$ bicycloheteroalkyl-$C_{1-3}$-alkyl, and $C_{6-10}$-tricycloheteroalkyl-$C_{1-3}$-alkyl, which are optionally substituted with 1-5 substituents chosen from methyl, ethyl, hydroxy, amino and fluoro, aryl and heteroaryl, which are optionally substituted with 1-5 substituents Y as defined above, aryl-$C_{1-5}$-alkyl, heteroaryl-$C_{1-15}$-alkyl, and di(hetero)aryl-$C_{1-5}$-alkyl group, wherein the phenyl and heteroaromatic rings are optionally substituted with 1-5 substituents Y as defined above, linear and branched $C_{4-8}$ alkenyl, and $C_{4-8}$ alkynyl which are optionally substituted with 1-3 fluorine atoms, with the proviso that when n=1, $R_3$ is chosen from branched and linear $C_{2-10}$ heteroalkyl, containing 1-2 heteroatoms chosen from N, O, and S;

$R_5$ is chosen from hydrogen and $C_{1-2}$ alkyl group, which are optionally substituted with 1-3 fluorine atoms; and $R_6$ is $C_{1-2}$ alkyl, which is optionally substituted with 1-3 fluorine atoms.

In another embodiment, the invention relates to compounds of formula (I):

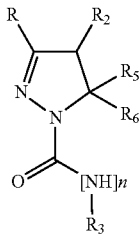

(I)

or a tautomer, stereoisomer, N-oxide, isotopically-labelled analogue, or a
pharmacologically acceptable salt of any of the foregoing, wherein:

$R_2$ is chosen from phenyl, thienyl, and pyridyl, which are optionally substituted with 1, 2, or 3 substituents Y as defined above.

In another embodiment, the invention relates to compounds of formula (I):

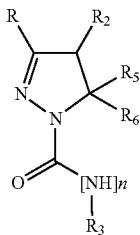

(I)

or a tautomer, stereoisomer, N-oxide, isotopically-labelled analogue, or a
pharmacologically acceptable salt of any of the foregoing, wherein:

n=1; and $R_2$ is chosen from phenyl, thienyl, and pyridyl, which are optionally substituted with 1, 2, or 3 substituents Y as defined above.

In another embodiment, the invention relates to compounds of formula (I):

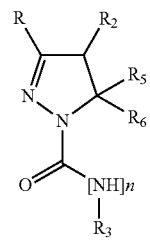

(I)

or a tautomer, stereoisomer, N-oxide, isotopically-labelled analogue, or a
pharmacologically acceptable salt of any of the foregoing, wherein:

n=1;

$R_2$ is chosen from phenyl, thienyl, and pyridyl, which are optionally substituted with 1, 2, or 3 substituents Y as defined above;

$R_5$ is chosen from hydrogen and methyl; and $R_6$ is methyl.

In another embodiment, the invention relates to compounds of formula (I):

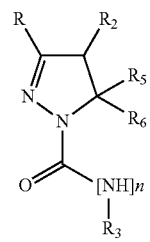

(I)

or a tautomer, stereoisomer, N-oxide, isotopically-labelled analogue, or a
pharmacologically acceptable salt of any of the foregoing, wherein:

n=1;

R is chosen from $C_{4-8}$ branched and $C_{3-8}$ linear alkyl, which are optionally substituted with 1-3 fluorine atoms;

$R_2$ is phenyl, which is optionally substituted with 1, 2, or 3 substituents Y as defined above;

$R_5$ is chosen from hydrogen and methyl; and $R_6$ is methyl.

In another embodiment, the invention relates to compounds of formula (I):

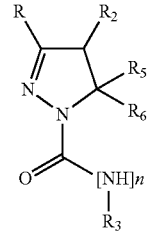

(I)

or a tautomer, stereoisomer, N-oxide, isotopically-labelled analogue, or a
pharmacologically acceptable salt of any of the foregoing, wherein:

n=1;

R is $C_{3-5}$ linear alkyl group;

$R_2$ is phenyl, which is optionally substituted with one or more halogens;

$R_5$ is chosen from hydrogen and methyl; and $R_6$ is methyl.

Further embodiments provide one or more compounds of formula (I):

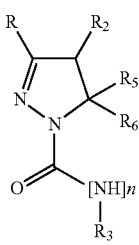

(I)

or a tautomer, stereoisomer, N-oxide, isotopically-labelled analogue, or a pharmacologically acceptable salt of any of the foregoing, having cannabinoid $CB_1$ receptor modulating activity. The compounds of the invention also have affinity for $CB_2$ receptors. They are useful in the treatment of disorders in which cannabinoid receptors are involved, or that can be treated via manipulation of those receptors In another embodiment, the invention relates to one or more compounds of the general formula (I), or pharmaceutically acceptable salts thereof, for the treatment of disorders in which cannabinoid receptors are involved, and in addition, that can be treated via manipulation of cannabinoid receptors.

Other embodiments of the invention include, but are not limited to:

pharmaceutical compositions for treating, for example, a disorder or condition that may be treated by modulating cannabinoid $CB_1$ receptors, the compositions comprising a compound of formula (I) or a pharmaceutically acceptable salt thereof, and a pharmaceutically acceptable carrier;

methods of treatment of a disorder or condition that may be treated by modulating cannabinoid $CB_1$ receptors, the methods comprising administering to a mammal in need of such treatment a compound of formula (I) or a pharmaceutically acceptable salt thereof;

pharmaceutical compositions for treating, for example, a disorder or condition selected from the group consisting of psychosis, anxiety, depression, attention deficits, memory disorders, cognitive disorders, appetite disorders, obesity, addiction, appetence, drug dependence, neurodegenerative disorders, dementia, dystonia, muscle spasticity, tremor, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including chronic pain, neuropathic pain, acute pain and inflammatory pain, osteoporosis, septic shock, glaucoma, diabetes, emesis, nausea, gastrointestinal disorders, gastric ulcers, diarrhea, sexual disorders, impulse control disorders and cardiovascular disorders;

methods of treatment of a disorder or condition selected from the group consisting of the disorders listed herein, the methods comprising administering to a mammal in need of such treatment a compound of formula (I) or a pharmaceutically acceptable salt thereof;

pharmaceutical compositions for treatment of a disorder or condition selected from the group consisting of the disorders listed herein, the compositions comprising a compound of formula (I) or a pharmaceutically acceptable salt thereof, and a pharmaceutically acceptable carrier;

methods of treatment of a disorder or condition that may be treated by modulating cannabinoid $CB_1$ receptors, the methods comprising administering to a patient in need of such treatment a compound of formula (I) or a pharmaceutically acceptable salt thereof; and methods of antagonizing a cannabinoid $CB_1$ receptor, which comprises administering to a subject in need thereof, an effective amount of a compound of formula (I);

The invention also provides the use of a compound or salt according to formula (I) for the manufacture of a medicament.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed. Such other therapeutic agent(s) may be administered prior to, simultaneously with, or following the administration of the compounds of the invention.

The invention also provides compounds, pharmaceutical compositions, kits and methods for the treatment of a disorder or condition that may be treated by modulating cannabinoid $CB_1$ receptors, the method comprising administering to a patient in need of such treatment a compound of formula (I) or a pharmaceutically acceptable salt thereof.

The compounds of the invention possess cannabinoid $CB_1$ receptor modulating activity. The (ant)agonizing activities of the compounds of the invention are readily demonstrated, for example, using one or more of the assays described herein or known in the art.

The invention also provides methods of preparing the compounds of the invention and the intermediates used in those methods.

The compounds of the present invention may contain one or more asymmetric centers and can thus occur as racemates and racemic mixtures, single enantiomers, diastereomeric mixtures and individual diastereomers.

All compounds of the present invention do contain at least one chiral centre (at the 4-position of the 4,5-dihydropyrazole ring). Additional asymmetric centers may be present depending upon the nature of the various substituents on the molecule. Each such asymmetric center will independently produce two optical isomers, and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base, such as for example (−)-di-p-toluoyl-D-tartaric acid and/or (+)-di-p-toluoyl-L-tartaric acid The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

Cis and trans isomers of the compound of formula (I) or a pharmaceutically acceptable salt thereof are also within the scope of the invention, and this also applies to tautomers of the compounds of formula (I) or a pharmaceutically acceptable salt thereof.

Some of the crystalline forms for the compounds may exist as polymorphs, and as such are intended to be included in the present invention.

Isotopically-labeled compounds of formula (I) or pharmaceutically acceptable salts thereof, including compounds of formula (I) isotopically-labeled to be detectable by PET or SPECT, are also included within the scope of the invention, and same applies to compounds of formula (I) labeled with [$^{13}$C]-, [$^{14}$C]-, [$^{3}$H]-, [$^{18}$F]-, [$^{125}$I]- or other isotopically enriched atoms, suitable for receptor binding or metabolism studies.

The compounds of the invention may also be used as reagents or standards in the biochemical study of neurological function, dysfunction and disease.

DEFINITIONS

General terms used in the description of compounds herein disclosed bear their usual meanings. The term alkyl as used herein denotes a univalent saturated, branched or straight, hydrocarbon chain. Unless otherwise stated, such chains can contain from 1 to 18 carbon atoms. Representative of such alkyl groups are methyl, ethyl, propyl, isopropyl, butyl, isobutyl, secbutyl, tert-butyl, pentyl, isopentyl, neopentyl, hexyl, isohexyl, heptyl, octyl, nonyl, decyl, undecyl, dodecyl, tridecyl, tetradecyl, pentadecyl, hexadecyl, heptadecyl, octadecyl, etc. When qualified lower 'lower', the alkyl group will contain from 1 to 6 carbon atoms. The same carbon content applies to the parent term 'alkane', and to derivative terms such as 'alkoxy'. The carbon content of various hydrocarbon containing moieties is indicated by a prefix designating the minimum and maximum number of carbon atoms in the moiety, i.e., the prefix $C_{x-y}$ defines the number of carbon atoms present from the integer "x" to the integer "y" inclusive. 'Alkyl($C_{1-3}$)' for example, means methyl, ethyl, n-propyl or isopropyl, and 'alkyl($C_{1-4}$)' means 'methyl, ethyl, n-propyl, isopropyl, n-butyl, 2-butyl, isobutyl or tert-butyl'. The term 'alkenyl' denotes straight or branched hydrocarbon radicals having one or more carbon-carbon double bonds, such as vinyl, allyl, butenyl, etc., and for example represents ($C_{2-4}$) alkenyl. In 'alkynyl' groups the straight or branched hydrocarbon radicals have one or more carbon-carbon triple bonds, such as ethynyl, propargyl, 1-butynyl, 2-butynyl, etc., and for example represent ($C_{2-4}$)alkynyl. Unless otherwise stated, 'alkenyl' and 'alkynyl' chains can contain from 1 to 18 carbon atoms.

The term 'acyl' means alkyl($C_{1-3}$) carbonyl, arylcarbonyl or aryl-alkyl($C_{1-3}$)carbonyl. 'Aryl' embraces mono- or polycyclic aromatic groups, including phenyl, naphthyl, 1,2,3,4-tetrahydro-naphtyl, indenyl, fluorenyl, anthracenyl, phenanthrenyl, naphthacenyl and azulenyl. 'Heteroaryl' embraces mono- or polycyclic hetero-aromatic, including furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, indazolyl, indolyl, indolizinyl, isoindolyl, benzo[b]furanyl, 1,2,3,4-tetrahydroiso-quinolinyl, indanyl, indenyl, benzo[b]thienyl, 2,3-dihydro-1,4-benzodioxin-5-yl, benzimidazolyl, cinnolinyl, carbazolyl, acridinyl, phenazinyl, phenothiazinyl, phenoxazinyl, benzothiazolyl, benzo[1,2,5]thia-diazolyl, purinyl, quinolinyl, isoquinolinyl, quinolizinyl, phtalazinyl, quinazolinyl, quinoxalinyl, 1,8-naphthyridinyl and pteridinyl.

'Halo' or 'Halogen' means chloro, fluoro, bromo or iodo; 'hetero' as in 'heteroalkyl, heteroaromatic' etc. means containing one or more N, O or S atoms. 'heteroalkyl' includes alkyl groups with heteroatoms in any position, thus including N-bound O-bound or S-bound alkyl groups.

The term "substituted" means that the specified group or moiety bears one or more substituents. Where any group may carry multiple substituents, and a variety of possible substituents is provided, the substituents are independently selected, and need not to be the same. The term "unsubstituted" means that the specified group bears no substituents. With reference to substituents, the term "independently" means that when more than one of such substituents are possible, they may be the same or different from each other.

'$C_{3-8}$-cycloalkyl' means cyclopropyl, cyclobutyl, cyclopentyl, cyclohexyl, cycloheptyl or cyclooctyl; '$C_{5-8}$ heterocycloalkyl' refers to heteroatom containing rings including piperidinyl, morpholinyl, azepanyl, pyrrolidinyl, thiomorpholinyl, piperazinyl, tetrahydrofuryl, tetrahydropyranyl; '$C_{5-10}$ bicycloalkyl group' refers to carbo-bicyclic ring systems including bicyclo[2.2.1]heptanyl, bicyclo[3.3.0]octanyl or the bicyclo[3.1.1]heptanyl group; '$C_{6-10}$-tricycloalkyl group' refers to carbo-tricyclic ring systems including 1-adamantyl, noradamantyl and 2-adamantyl groups. The abbreviation '$C_{8-11}$ tetracycloalkyl group' refers to carbo-tetracyclic ring systems including cubyl, homocubyl and bishomocubyl groups.

The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

To provide a more concise description, the terms 'compound' or 'compounds' include tautomers, stereoisomers, N-oxides, isotopically-labelled analogues, or pharmacologically acceptable salts, also when not explicitly mentioned.

As used herein, the term "leaving group" (L) shall mean a charged or uncharged atom or group that departs during a substitution or displacement reaction. The term refers to groups readily displaceable by a nucleophile, such as an amine, a thiol or an alcohol nucleophile. Such leaving groups are well known in the art. Examples include N-hydroxysuccinimide, N-hydroxybenzotriazole, halides (Br, Cl, I), triflates, mesylates, tosylates, etc.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertiary amines, or less active. Whilst N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

'Form' is a term encompassing all solids: polymorphs, and amorphous forms. 'Crystal form' refers to various solid forms of the same compound, for example polymorphs and amorphous forms. 'Cocrystals' are multicomponent crystals with a unique lattice: new chemical species produced with neutral compounds. 'Amorphous forms' are non-crystalline materials with no long range order, and generally do not give a distinctive powder X-ray diffraction pattern. Crystal forms in general have been described by Byrn (1995) and Martin (1995). 'Polymorphs' are crystal structures in which a compound can crystallize in different crystal packing arrangements, all of which have the same elemental composition. Polymorphism is a frequently occurring phenomenon, affected by several crystallization conditions such as temperature, level of supersaturation, the presence of impurities, polarity of solvent, rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to experimental or measurement conditions for such given value.

Throughout the description and the claims of this specification the word "comprise" and variations of the word, such as "comprising" and "comprises" is not intended to exclude other additives, components, integers or steps.

While it may be possible for the compounds of formula (I) to be administered as the raw chemical, in at least one embodiment, they are presented in a 'pharmaceutical composition'. According to a further aspect, the present invention provides a pharmaceutical composition comprising at least one compound of formula (I), at least one pharmaceutically acceptable salt, or a mixture of any of the foregoing, together with one or more pharmaceutically acceptable carriers thereof, and with or without one or more other therapeutic ingredients. The carrier(s) must be 'acceptable' in the sense of being compatible with the other ingredients of the formulation and not deleterious to the recipient thereof. The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The affinity of the compounds of the invention for cannabinoid $CB_1$ receptors was determined as described below. From the binding affinity measured for a given compound of formula (I), one can estimate a theoretical lowest effective dose. At a concentration of the compound equal to twice the measured $K_i$-value, nearly 100% of the cannabinoid $CB_1$ receptors likely will be occupied by the compound. Converting that concentration to mg of compound per kg of patient, yields a theoretical lowest effective dose, assuming ideal bioavailability.

Pharmacokinetic, pharmacodynamic, and other considerations may alter the dose actually administered to a higher or lower value. The typical daily dose of the active ingredients varies within a wide range and will depend on various factors such as the relevant indication, the route of administration, the age, weight and sex of the patient, and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance. A "pharmaceutical salt" is an acid:base complex containing an active pharmaceutical ingredient (API) along with additional non-toxic molecular species in the same crystal structure. The term "pharmaceutically acceptable salt" refers to those salts that are, within the scope of sound medical judgment, suitable for use in contact with the tissues of humans and lower animals without undue toxicity, irritation, allergic response, etc., and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, 1977). Common anions used in pharmaceutically acceptable salts include: chloride, bromide, sulfate, nitrate, phosphate, bicarbonate, mesylate, esylate, isothianate, tosylate, napsylate, besylate, acetate, propionate, maleate, benzoate, salicylate, fumarate, citrate, lactate, maleate, tartrate, pamoate, succinate, glycolate, hexanoate, octanoate, decanoate, stearate, oleate, aspartate and glutamate. Common cations used as counterions in pharmaceutically acceptable salts include: sodium, potassium, calcium, magnesium, lithium, zinc, aluminum, arginine, lysine, histidine, triethylamine, ethanolamine, triethanolamine, ethilenediamine, meglumine, procaine and benzathine.

The 'free base' form may be regenerated by contacting the salt with a base or acid, and isolating the parent compound in the conventional matter. The parent form of the compound differs from the various salt forms in certain physical properties, such as solubility in polar solvents, but otherwise the salts are equivalent to the parent form of the compound for the purposes of the present invention. 'Complex' refers to a complex of the compound of the invention, e.g. formula (I), complexed with a metal ion, where at least one metal atom is chelated or sequestered. Complexes are prepared by methods well known in the art (Dwyer, 1964).

The term "treatment" as used herein refers to any treatment of a mammalian, for example human condition or disease, and includes: (1) inhibiting the disease or condition, i.e., arresting its development, (2) relieving the disease or condition, i.e., causing the condition to regress, or (3) stopping the symptoms of the disease. The term 'inhibit' includes its generally accepted meaning which includes prohibiting, preventing, restraining, alleviating, ameliorating, and slowing, stopping or reversing progression, severity, or a resultant symptom. As such, the present method includes both medical therapeutic and/or prophylactic administration, as appropriate. As used herein, the term "medical therapy" intendeds to include prophylactic, diagnostic and therapeutic regimens carried out in vivo or ex vivo on humans or other mammals. 'Mammals' include animals of economic importance such as bovine, ovine, and porcine animals, especially those that produce meat, as well as domestic animals, sports animals, zoo animals, and in at least one embodiment humans. The term "subject" as used herein, refers to an animal, in at least one embodiment, a mammal, for example a human, who has been the object of treatment, observation or experiment.

| ABBREVIATIONS | |
|---|---|
| ACN | acetonitrile |
| API | active pharmaceutical ingredient |
| API-ES | atmospheric pressure ionization - electron spray |
| BOC | tert-butoxycarbonyl |
| BSA | bovine serum albumin |
| $CB_1$ | cannabinoid receptor subtype-1 |
| $CB_2$ | cannabinoid receptor subtype-2 |
| CHO | Chinese Hamster Ovary (cells) |
| CNS | central nervous system |
| CUR | curtain gas |
| DF | deflector voltage |
| DIPEA | N,N-diisopropylethylamine |
| DMAP | 4-dimethylaminopyridine |

-continued

| ABBREVIATIONS | |
|---|---|
| DMEM | Dulbecco's Modified Eagle's Medium |
| DMF | N,N'-dimethylformamide |
| DMSO | dimethylsulfoxide |
| DSC | differential scanning calorimetry |
| EDCl | 1-(3-dimethylaminopropyl)-3-ethylcarbodiimide hydrochloride |
| EP | entrance potential |
| $Et_3N$ | triethylamine |
| FP | focusing potential |
| g | gram(s) |
| h | hour(s) |
| HOBt | N-hydroxybenzotriazole |
| HPLC | high performance liquid chromatography |
| IBMX | 3-isobutyl-1-methylxanthine |
| IS | ionspray voltage |
| MeOH | methanol |
| mg | milligram(s) |
| min | minute(s) |
| ml | milliliter(s) |
| m.p. | melting point c.q. melting range |
| MTBE | methyl tert-butylether |
| NBS | N-bromosuccinimide |
| NEB | nebulizer gas |
| NMM | N-methylmorpholine |
| NMR-NOE | nuclear magnetic resonance-nuclear Overhauser effect |
| PBS | phosphate buffered saline |
| PET | positron emission tomography |
| $R_f$ | retention factor (thin layer chromatography) |
| $R_t$ | retention time (LC/MS) |
| RT | room temperature |
| SPECT | single photon emission computed tomography |
| TEM | temperature |
| THF | tetrahydrofuran |

EXAMPLES

Example 1

Materials and Methods $^1$H NMR spectra were recorded on either a Varian 300 MHz instrument, a Varian UN400 instrument (400 MHz) using DMSO-$d_6$ or CDCl$_3$ as solvents with tetramethylsilane as an internal standard. $^{13}$C NMR spectra were recorded on a Varian UN400 instrument using CDCl$_3$ as solvent. Chemical shifts are given in ppm (δ scale) downfield from tetramethylsilane. Coupling constants (J) are expressed in Hz. Flash chromatography was performed using silica gel 60 (0.040-0.063 mm, Merck).

Column chromatography was performed using silica gel 60 (0.063-0.200 mm, Merck). Sepacore chromatographic separations were carried out using Supelco equipment, VersaFLASH™ columns, VersaPak™ silica cartridges, Büchi UV monitor C-630, Büchi Pump module C-605, Büchi fraction collector C-660 and Büchi pump manager C-615.

Melting points were recorded on a Büchi B-545 melting point apparatus or determined by DSC methods.

Optical rotations ($[α]_D$) were measured on an Optical Activity polarimeter. Specific rotations are given as deg/dm, the concentration values are reported as g/100 mL of the specified solvent and were recorded at 23° C.

Example 2

General Aspects of Syntheses

Pyrazoline derivatives can be obtained by published methods (Barluenga, 1999 (and references cited therein); Wang, 2003). The synthesis of compounds having formula (I) is outlined in Scheme 1. Ketone derivatives of general formula (II) can be made by various methods known to those skilled in the art. Examples are the application of a Weinreb amide $RC(=O)N(OCH_3)CH_3$ which can be reacted with a Grignard reagent $R_2CH_2MgCl$ or $R_2CH_2MgBr$ or a reaction of RMgBr or RMgCl with a Weinreb amide of general formula $R_2CH_2C(=O)N(OCH_3)CH_3$. Alternatively, a Grignard reagent $R_2CH_2MgCl$ or $R_2CH_2MgBr$ can be reacted with HCN, followed by acidic hydrolysis, for example by using hydrochloric acid. A ketone derivative of general formula (II) wherein R and $R_2$ have the abovementioned meaning can be reacted with a halogenide derivative of general formula $R_5R_6CHI$ in the presence of a base, such as sodium methoxide to give a compound of general formula (IIa), wherein R, $R_2$, $R_5$ and $R_6$ have the abovementioned meaning. The compound of general formula (IIa) can be reacted with a brominating agent such as N-bromosuccinimide (NBS), preferably in the presence of a radical initiator such as dibenzoyl peroxide in an inert organic solvent such as carbon tetrachloride to give a compound of formula (IIb), wherein R, $R_2$, $R_5$ and $R_6$ have the abovementioned meaning. The compound of general formula (IIb) can be reacted in an elimination reaction with lithium chloride at elevated temperature in an organic solvent such as dimethylformamide to give a compound of formula (III), wherein R, $R_2$, $R_5$ and $R_6$ have the abovementioned meaning. The enone derivative of general formula (III) can be reacted with hydrazine, a hydrazine salt or hydrazine hydrate to give a 4,5-dihydropyrazole derivative of formula (IV).

A compound of formula (IV) can be reacted with a carboxylic acid $R_3$—$CO_2H$ wherein $R_3$ has the abovementioned meaning in the presence of an 'activating reagent' or coupling reagent in an inert organic solvent such as dichloromethane to give a pyrazoline derivative of general formula (I), wherein n=0 and all other symbols have the meanings as given above. Additional information on activating and coupling methods of amines to carboxylic acids can be found in the literature (Bodanszky, 1994; Akaji, 1994; Albericio, 1997; Montalbetti, 2005).

Alternatively, a compound of formula (IV) wherein R, $R_2$, $R_5$ and $R_6$ have the abovementioned meaning can be reacted with an acid chloride $R_3$—COCl wherein $R_3$ has the abovementioned meaning to give a pyrazoline derivative of general formula (I), wherein n=0 and all other symbols have the meanings as given above. Such a reaction is preferably carried out in the presence of a base such as triethylamine or DIPEA (Hünig's base).

A compound of formula (IV) wherein R, $R_2$, $R_5$ and $R_6$ have the abovementioned meaning can be reacted with an isocyanate derivative $R_3$—N=C=O (VII) wherein $R_3$ has the abovementioned meaning in the presence of an inert organic solvent such as diethyl ether to give a pyrazoline-1-carboxamide derivative of general formula (I), wherein n=1 and all other symbols have the meanings as given above. Isocyanates $R_3$—N=C=O can also be prepared in situ from the corresponding amine $R_3$—$NH_2$ and a carbonyl donor such as phosgene, diphosgene (trichloromethyl chloroformate) or triphosgene (bis(trichloromethyl)carbonate). Alternatively, isocyanates $R_3$—N=C=O can be prepared from the corresponding carboxylic acid $R_3$—COOH via the acylazide $R_3$—$CON_3$ in a Curtius rearrangement.

Alternatively, a Weinreb amide of general formula (IIIa) (which can be obtained from the corresponding acrylic acid derivatives according to methods well known to those skilled in the art) wherein $R_5$ and $R_6$ have the abovementioned meaning can be reacted with a Grignard reagent of formula RMgBr wherein R has the abovementioned meaning in the presence of an inert organic solvent such as tetrahydrofuran, to give a ketone derivative of formula (IIIb). Compounds of formula (IIIb) can also be prepared from a Weinreb amide of general formula R—C(=O)—$N(OCH_3)CH_3$ and an olefinic Grignard reagent of general formula $R_5R_6C$=CHMgBr wherein $R_5$ and $R_6$ have the abovementioned meaning. The resulting ketone derivative of general formula (IIIb) can be brominated at its olefinic bond with bromine in the presence of an inert organic solvent such as dichloromethane, followed by reaction with a base such as triethylamine to afford a compound of general formula (IIIc) in a so-called one-pot reaction. The compound of general formula (IIIc) can be reacted in a transition metal-catalyzed cross-coupling reaction, such as the so-called Suzuki-Miyaura reaction (Miyaura, 1995) with a compound of general formula $R_2$—$B(OH)_2$ in the presence of a palladium-based catalyst such as $Pd(OAc)_2$ and a suitable ligand, such as X-Phos, Ruphos or S-Phos and the like to give a compound of general formula (III), wherein R, $R_2$, $R_5$ and $R_6$ have the abovementioned meaning.

Scheme 1

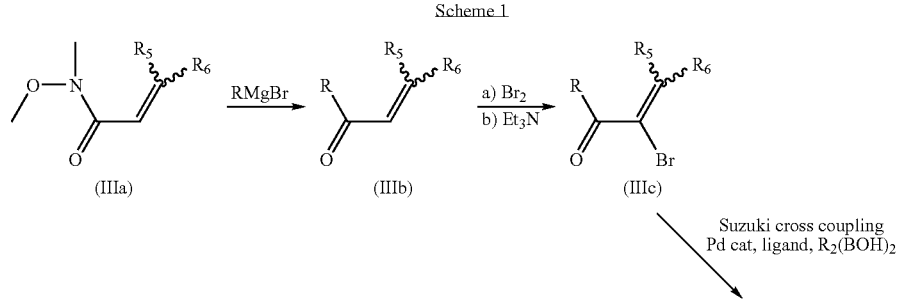

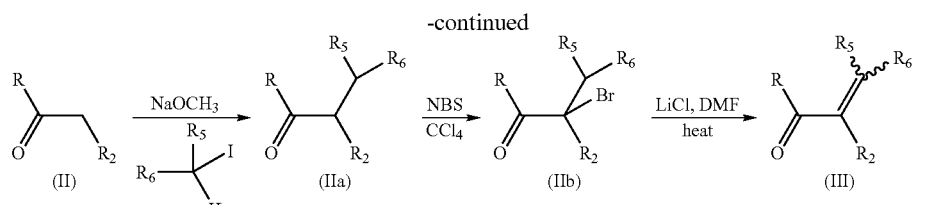

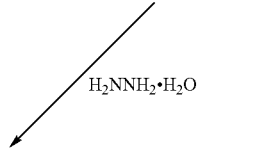

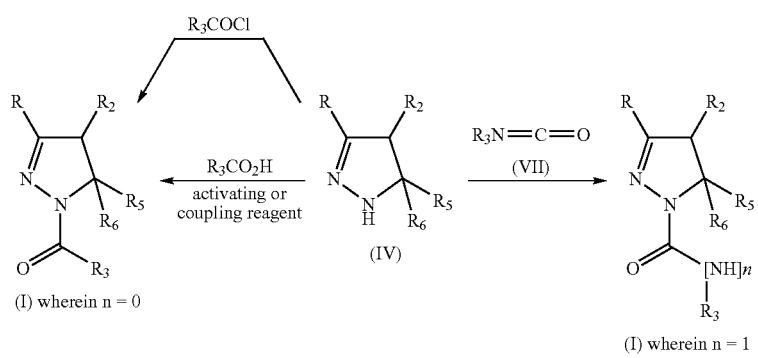

Alternatively, a compound of formula (IV), wherein R, $R_2$, $R_5$ and $R_6$ have the abovementioned meaning can be reacted with phosgene, diphosgene or triphosgene to give a compound of formula (VIII) wherein R and $R_2$ have the abovementioned meaning (Scheme 2). Such a reaction is preferably carried out in the presence of a base such as triethylamine or DIPEA (Hünig's base). A compound of formula (VIII) can be reacted in an inert solvent such as dichloromethane with a compound $NH_2R_3$ to give a pyrazoline-1-carboxamide derivative of formula (I), wherein n=1.

Scheme 2

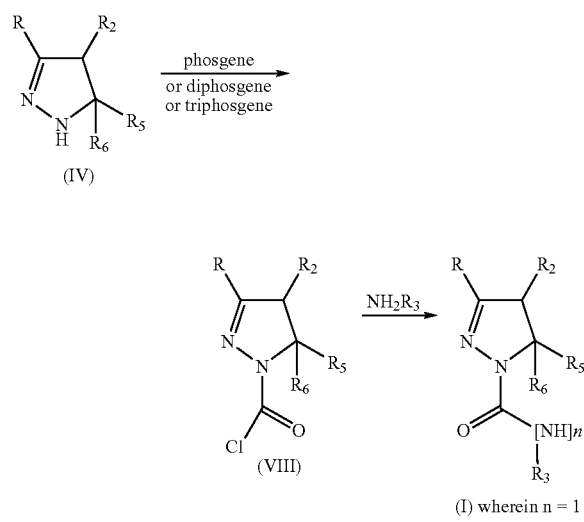

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Compounds of the general formula (III) wherein R is chosen from phenyl, pyridyl or thienyl, optionally substituted with 1-3 substituents Y1 wherein Y1 is chosen from halogen, methyl, $CF_3$, $OCF_3$ or $OCH_3$, and $R_2$ is chosen from a n-propyl, n-butyl, n-pentyl, 1,1-dimethylpropyl, 1,1-dimethylbutyl, 3,3,3-trifluoropropyl, 4,4,4-trifluorobutyl or 1,1-dimethyl-3,3,3-trifluoropropyl group are new. Such compounds are useful in the synthesis of compounds of the general formula (I).

Compounds of formula (IV) wherein R, $R_2$, $R_5$ and $R_6$ have the same meanings as given above are new. Such compounds are useful in the synthesis of compounds of formula (I).

Compounds of formula (VIII) wherein R, $R_2$, $R_5$ and $R_6$ have the same meanings as given above, are new. They are useful at synthesizing compounds of formula (I) wherein n=1.

Pharmaceutically acceptable salts may be obtained using standard procedures well known in the art, e.g. by mixing a compound of the present invention with a suitable acid, for instance an inorganic acid such as hydrochloric acid, or with an organic acid such as fumaric acid. According to these procedures the compounds described below have been prepared. They are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

Example 3

Synthesis and Spectral Data of Intermediates

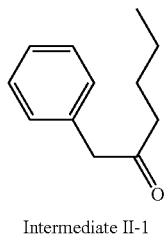

Intermediate II-1

Part A: To a magnetically stirred solution of valeric acid (10.9 ml, 0.1 mol) in dichloromethane (200 ml) was successively added: N-methyl-N-methoxy-amine.hydrochloride (10.14 gram, 0.104 mol), N-methylmorpholine (22.9 ml, 0.208 mol), 1-(3-dimethylaminopropyl)-3-ethylcarbodiimide.HCl (EDCI) (19.92 gram, 0.104 mol) and HOBt (14.04 gram, 0.104 mol) and the resulting mixture was reacted for 20 hours at room temperature. The obtained suspension was successively washed with water, aqueous citric acid (a solution of 24 gram citric acid in 250 ml $H_2O$) and 5% aqueous $NaHCO_3$. The organic layer was dried over $Na_2SO_4$, filtered and concentrated to give pentanoic acid methoxy-methyl-amide (12.31 gram, 85% yield) as a colorless oil. $^1$H-NMR (400 MHz, $CDCl_3$) δ 0.93 (t, J=7, 3H), 1.31-1.43 (m, 2H), 1.57-1.66 (m, 2H), 2.42 (br t, J=7, 2H), 3.18 (s, 3H), 3.69 (s, 3H).

Part B: To a magnetically stirred solution of pentanoic acid methoxy-methyl-amide (8.6 g, 59.3 mmol) at 0° C. in anhydrous THF (100 ml) was slowly added benzylmagnesium chloride (2 M solution in THF, 45 ml, 90 mmol) and the resulting mixture was reacted for 20 hours in a nitrogen atmosphere at room temperature. The reaction mixture was poured in excess of a cold (0° C.) aqueous hydrochloric acid (4 N solution) and extracted with MTBE. The organic layer was dried over $Na_2SO_4$, filtered and concentrated to give crude product. This crude product was further purified using Sepacore equipment: Gradient: (petroleum ether/diethyl ether=98/2 (v/v))=>(petroleum ether/diethyl ether=95/5 (v/v)) to give 1-phenylhexan-2-one (Intermediate II-1) (7.38 gram, 71% yield) as a colorless oil; $^1$H-NMR (400 MHz, $CDCl_3$) δ 0.86 (t, J=7, 3H), 1.21-1.31 (m, 2H), 1.48-1.58 (m, 2H), 2.41-2.47 (m, 2H), 3.68 (s, 2H), 7.18-7.36 (m, 5H).

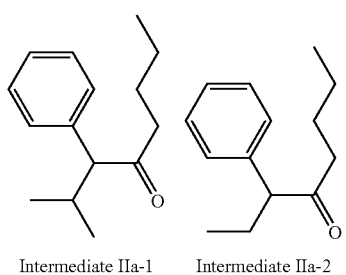

Intermediate IIa-1     Intermediate IIa-2

To an ice-cold magnetically stirred mixture of 1-phenyl-hexan-2-one (Intermediate II-1) (7.04 gram, 0.04 mol) and sodium methoxide (4.32 g, 0.08 mol) was added dropwise 2-iodopropane (15 ml) in a nitrogen atmosphere. The resulting mixture was heated for 1 hour at reflux temperature. The obtained mixture was allowed to attain room temperature and concentrated. The resulting residue was taken up in diethyl ether and water. The diethyl ether layer was separated and successively washed with an aqueous $Na_2S_2O_3$ solution and water. The organic layer was dried over $Na_2SO_4$, filtered and concentrated. The residue was further purified using Sepacore equipment: (petroleum ether/diethyl ether=19/1 (v/v)) to give 2-methyl-3-phenyl-octan-4-one (Intermediate IIa-1) (3.52 gram) as a colorless oil; $^1$H-NMR (400 MHz, $CDCl_3$) δ 0.66 (d, J=7, 3H), 0.81 (t, J=7, 3H), 0.96 (d, J=7, 3H), 1.10-1.24 (m, 2H), 1.36-1.54 (m, 2H), 2.29-2.47 (m, 3H), 3.30 (d, J=10 Hz, 1H), 7.20-7.33 (m, 5H). $R_f$ (petroleum ether/diethyl ether=98/2 (v/v))~0.25.

Analogously, 3-phenyloctan-4-one (intermediate IIa-2) was prepared from 1-phenylhexan-2-one (Intermediate II-1), sodium methoxide and iodoethane in 60% yield. $^1$H-NMR (400 MHz, $CDCl_3$) δ 0.81 (d, J=7, 3H), 0.83 (t, J=7, 3H), 1.11-1.24 (m, 2H), 1.38-1.55 (m, 2H), 1.64-1.76 (m, 1H), 2.00-2.11 (m, 1H), 2.28-2.42 (m, 2H), 3.53 (t, J=7 Hz, 1H), 7.18-7.26 (m, 3H), 7.28-7.34 (m, 3H).

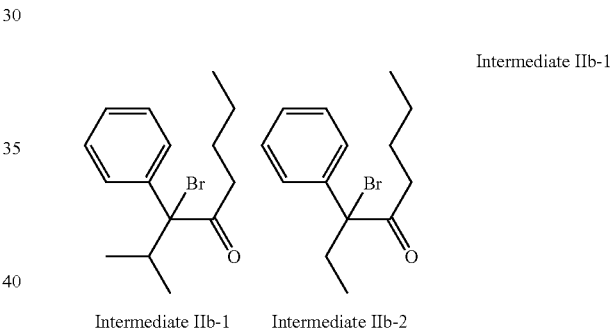

Intermediate IIb-1     Intermediate IIb-2

To a magnetically stirred solution of 2-methyl-3-phenyloctan-4-one (Intermediate IIa-1) (4.31 gram, 0.02 mol) in $CCl_4$ (40 ml) was added a catalytic amount of dibenzoyl peroxide and NBS (6.56 gram). The resulting mixture was heated for 6 hours at reflux temperature. The obtained mixture was allowed to attain room temperature. The formed precipitate was removed by filtration. The filtrate was concentrated to give crude 2-methyl-3-bromo-3-phenyloctan-4-one (intermediate IIb-1)—contaminated with some starting material—as a dark-colored oil (6.77 gram). $^1$H-NMR (400 MHz, $CDCl_3$) Characteristic signals: δ 0.68 (d, J=6, 3H), 0.78 (t, J=7, 3H), 1.08 (d, J=6, 3H).

Analogously, 3-bromo-3-phenyloctan-4-one (intermediate IIb-2) was prepared in 74% yield from 3-phenyloctan-4-one (Intermediate IIa-2), dibenzoyl peroxide and NBS in $CCl_4$. $R_f$ (petroleum ether/diethyl ether=99/1 (v/v))=0.2. $^1$H-NMR (400 MHz, $CDCl_3$) δ 0.81 (t, J=7, 3H), 0.84 (t, J=7, 3H), 1.14-1.24 (m, 2H), 1.41-1.62 (m, 2H), 2.20-2.47 (m, 3H), 2.65-2.75 (m, 1H), 7.29-7.43 (m, 5H).

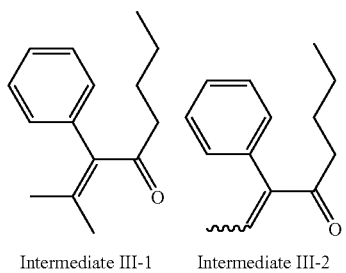

Intermediate III-1

Intermediate III-1  Intermediate III-2

The crude 2-methyl-3-bromo-3-phenyloctan-4-one (intermediate IIb-1) was dissolved in magnetically stirred anhydrous DMF (35 ml) under a nitrogen atmosphere. Lithium chloride (3.2 gram, 0.075 mol) was added and the resulting mixture was heated at 130° C. for 90 minutes. The resulting mixture was allowed to attain room temperature and was subsequently poured into water and extracted with diethyl ether. The organic layer was separated and washed with water (4 portions). The organic layer was dried over $Na_2SO_4$, filtered and concentrated. The obtained residue was purified using Sepacore equipment: (petroleum ether/diethyl ether=98/2 (v/v)) to give 2-methyl-3-phenyloct-2-en-4-one (Intermediate III-1) (1.96 gram, 46% yield) as a pale yellow oil; $^1$H-NMR (400 MHz, $CDCl_3$) δ 0.81 (d, J=7, 3H), 1.13-1.24 (m, 2H), 1.43-1.52 (m, 2H), 1.66 (s, 3H), 2.00 (s, 3H), 2.25 (t, J=7, 2H), 7.15 (br d, J=8, 2H), 7.20-7.39 (m, 3H).

Analogously 3-phenyloct-2-en-4-one (Intermediate III-2; one stereoisomer) was prepared from 3-bromo-3-phenyloctan-4-one (intermediate IIb-2) and LiCl in DMF in 57% yield using Sepacore equipment: (petroleum ether/diethyl ether=97/3 (v/v)). $R_f$ (petroleum ether/diethyl ether=95/5 (v/v))~0.15. $^1$H-NMR (400 MHz, $CDCl_3$) δ 0.87 (d, J=7, 3H), 1.23-1.34 (m, 2H), 1.52-1.61 (m, 2H), 1.72 (d, J=7, 3H), 2.53 (t, J=7, 2H), 6.97 (q, J=7, 1H), 7.10 (br d, J=8, 2H), 7.29-7.41 (m, 3H).

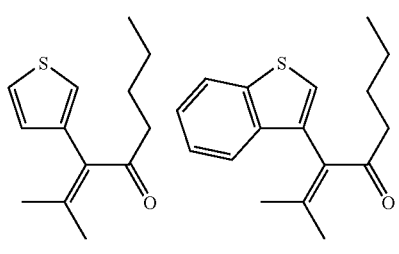

Intermediate III-3

Intermediate III-3  Intermediate III-4

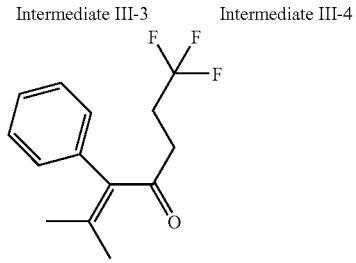

Intermediate III-5

To a magnetically stirred solution of 3-bromo-2-methyl-oct-2-en-4-one (5 gram, 20.54 mmol) (Intermediate IIIc-1) in nitrogen-degassed n-butanol (50 ml) was successively added thiophene-3-boronic acid (3.94 gram, 30.80 mmol), palladium(II)acetate (46.11 mg, 0.21 mmol), 2-dicyclohexylphosphino-2',6'-dimethoxy-1,1'-biphenyl (S-Phos) (168.6 mg, 0.41 mmol) and $K_3PO_4$ (8.72 g, 41.07 mmol) and the resulting mixture was reacted at 100° C. for 2 hours. The mixture was concentrated in vacuo and purified by sepacore chromatography (40×150 mm column), eluant: (Gradient: eluant 1: petroleum ether (40-60); Eluant 2: petroleum ether (40-60)/diethyl ether=95/5 (v/v)) to give 3-(3-thienyl)-2-methyl-oct-2-en-4-one (2.80 gram, 55%). $^1$H-NMR (400 MHz, $CDCl_3$) δ 0.83 (t, J=7, 3H), 1.17-1.27 (m, 2H), 1.45-1.54 (m, 2H), 1.72 (s, 3H), 1.97 (s, 3H), 2.30 (t, J=7.4, 2H), 6.92 (br d, J=5, 1H), 7.04 (br d, J=3, 1H), 7.33 (dd, J=5 and 3, 1H).

Analogously, 3-(3-benzothienyl)-oct-2-en-4-one (Intermediate III-4) was prepared from 3-bromo-2-methyl-oct-2-en-4-one. $^1$H-NMR (400 MHz, $CDCl_3$) δ 0.75 (t, J=7, 3H), 1.08-1.19 (m, 2H), 1.39-1.50 (m, 2H), 1.63 (s, 3H), 2.14 (s, 3H), 2.20 (t, J=7.4, 2H), 7.21 (s, 1H), 7.36-7.41 (m, 2H), 7.56-7.59 (m, 1H), 7.88-7.92 (m, 1H).

Analogously, 7,7,7-trifluoro-3-phenyl-2-methyl-hept-2-en-4-one (Intermediate III-5) was prepared from intermediate IIIc-2 and phenylboronic acid (Ph-B(OH)$_2$). $^1$H-NMR (400 MHz, $CDCl_3$) δ 1.66 (s, 3H), 2.07 (s, 3H), 2.28-2.49 (m, 4H), 7.14 (d, J=8, 2H), 7.30-7.42 (m, 3H).

Using analogous methods the intermediates III-6-III-11 were also synthesized:

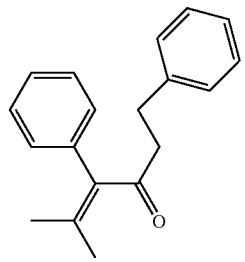

Intermediate III-6

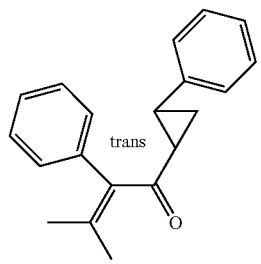

Intermediate III-7

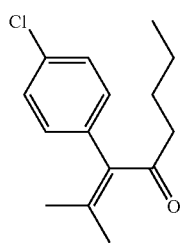

Intermediate III-8

-continued

Intermediate III-9

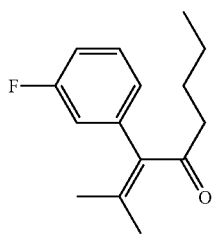

Intermediate III-10

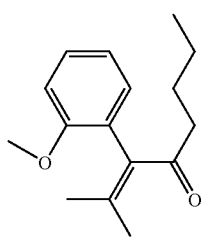

Intermediate III-11

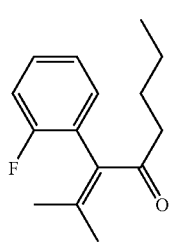

Intermediate III-6 (5-methyl-1,4-diphenyl-hex-4-en-3-one) was prepared from intermediate IIIc-3 and Ph-B(OH)$_2$. $^1$H-NMR (400 MHz, CDCl$_3$) δ 1.64 (s, 3H), 2.00 (s, 3H), 2.56 (t, J=7, 2H), 2.81 (t, J=7, 2H), 7.04 (d, J=8, 2H), 7.08-7.36 (m, 8H).

Intermediate III-7 (2-phenyl-3-methyl-1-(2-phenyl-trans-cyclopropyl)but-2-en-1-one) was from intermediate IIIc-4 and Ph-B(OH)$_2$. $^1$H-NMR (400 MHz, CDCl$_3$) δ 1.15-1.24 (m, 1H), 1.66-1.72 (m, 4H), 2.02-2.08 (m, 4H), 2.47-2.54 (m, 1H), 6.90 (br d, J=8, 2H), 7.08-7.34 (m, 8H).

Intermediate III-8 (2-methyl-3-(4-chlorophenyl)oct-2-en-4-one) was prepared from 2-methyl-3-bromo-oct-2-en-4-one and 4-chlorophenylboronic acid. $^1$H-NMR (400 MHz, CDCl$_3$) δ 0.82 (t, J=7.4, 3H), 1.14-1.25 (m, 2H), 1.43-1.53 (m, 2H), 1.66 (s, 3H), 2.00 (s, 3H), 2.24 (t, J=7.4, 2H), 7.09 (d, J=8, 2H), 7.33 (d, J=8, 2H). Intermediate III-9 (2-methyl-3-(3-fluorophenyl)oct-2-en-4-one) was prepared from 2-methyl-3-bromo-oct-2-en-4-one and 3-fluorophenylboronic acid. $^1$H-NMR (400 MHz, CDCl$_3$) δ 0.82 (t, J=7.4, 3H), 1.13-1.24 (m, 2H), 1.43-1.53 (m, 2H), 1.66 (s, 3H), 2.01 (s, 3H), 2.26 (t, J=7.4, 2H), 6.86-7.03 (m, 3H), 7.29-7.36 (m, 1H).

Intermediate III-10 (2-methyl-3-(2-methoxyphenyl)oct-2-en-4-one) was prepared from 2-methyl-3-bromo-oct-2-en-4-one and 2-methoxyphenylboronic acid. $^1$H-NMR (400 MHz, CDCl$_3$) δ 0.80 (t, J=7.4, 3H), 1.12-1.23 (m, 2H), 1.41-1.50 (m, 2H), 1.64 (s, 3H), 2.09 (s, 3H), 2.17 (t, J=7.2, 2H), 3.77 (s, 3H), 6.89 (d, J=8, 1H), 6.93-6.98 (m, 1H), 7.09 (dd, J=8 and 2, 1H), 7.27-7.33 (m, 1H).

Intermediate III-11 (2-methyl-3-(2-fluorophenyl)oct-2-en-4-one) was prepared 2-methyl-3-bromo-oct-2-en-4-one and 2-fluorophenylboronic acid. $^1$H-NMR (400 MHz, CDCl$_3$) δ 0.81 (t, J=7.4, 3H), 1.14-1.24 (m, 2H), 1.43-1.53 (m, 2H), 1.64 (s, 3H), 2.10 (s, 3H), 2.23 (t, J=7.4, 2H), 7.08-7.18 (m, 3H), 7.28-7.36 (m, 1H).

Intermediate IIIa-1

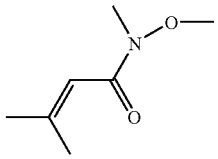

Intermediate IIIa-1

To a magnetically stirred solution of 3,3-dimethylacrylic acid (25.0 gram, 250 mmol) in dichloromethane (400 ml) were successively added N,O-dimethylhydroxylamine.hydrochloride (26.79 gram, 275 mmol), N-(3-dimethylaminopropyl)-N'-ethylcarbodiimide.hydrochloride (52.66 gram, 275 mmol) and 1-hydroxybenzotriazole (16.87 gram, 124.8 mmol). The mixture was cooled with an ice-bath and N-methylmorpholine (82.36 ml, 749 mmol) was added and the resulting mixture was stirred at room temperature for 20 hours. Water (100 ml) was added and the organic layer was separated, and successively washed with citric acid (0.5 M aqueous solution), NaHCO$_3$ (5% aqueous solution) and brine, dried over MgSO$_4$, filtered and concentrated to give N-methoxy-N-methyl-acrylamide (29.53 gram, 78.5% yield). $^1$H-NMR (400 MHz, CDCl$_3$) δ1.91 (d, J=2 Hz, 3H), 2.14 (d, J=2 Hz, 3H), 3.20 (s, 3H), 3.68 (s, 3H), 6.12 (br s, 1H).

Intermediate IIIb-1

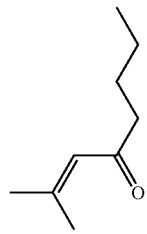

Intermediate IIIb-1

To a magnetically stirred and ice-cooled solution of N-methoxy-N-methyl-acrylamide (20 gram, 132.7 mmol) in anhydrous tetrahydrofuran (200 ml) in a nitrogen atmosphere was slowly added n-butylmagnesium chloride (132.7 ml, 2 M solution in diethyl ether, 265 mmol) and the resulting mixture was stirred for 30 minutes. The resulting mixture was allowed to attain room temperature and stirred for 40 hours. An aqueous ammonium chloride solution (15 gram dissolved in 100 ml water) was slowly added, followed by addition of ethyl acetate (100 ml). The organic layer was separated, washed with brine, dried over MgSO$_4$, filtered and concentrated in vacuo to give crude 2-methyl-oct-2-en-4-one. Sepacore (80× 150 mm column) separation (eluant: petroleum ether (40-60)/diethyl ether=95/5 (v/v)) gave 2-methyl-oct-2-en-4-one (Intermediate IIIb-1) as a colorless oil (9.30 gram, 47% yield). $^1$H-NMR (400 MHz, CDCl$_3$) δ 0.91 (t, J=7.2 Hz, 3H), 1.27-1.38 (M, 2H), 1.52-1.62 (m, 2H), 1.89 (s, 3H), 2.14 (s, 3H), 2.39 (t, J=7.4 Hz, 2H), 6.08 (br s, 1H).

Intermediates IIIb-2, IIIb-3 and IIIb-4

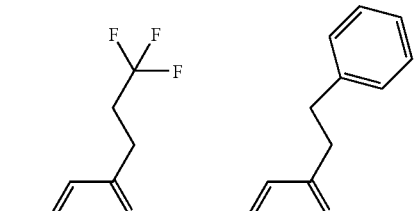

Intermediate IIIb-2     Intermediate IIIb-3

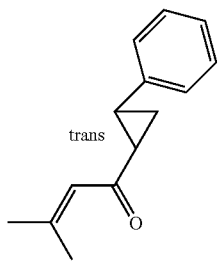

Intermediate IIIb-4

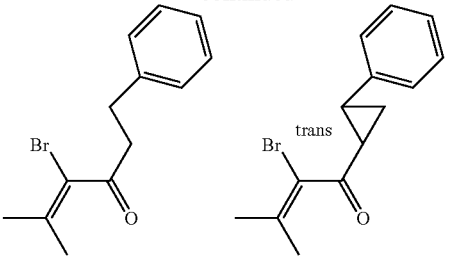

Intermediate IIIc-3    Intermediate IIIc-4

To a solution of 4,4,4-trifluoro-N-methoxy-N-methyl-butyramide (6.17 g; 33.3 mmol) in anhydrous THF (100 ml) at 0° C. was added dropwise 2-methyl-1-propenylmagnesium bromide (100 ml; 0.50 mol/l solution in THF; 50 mmol). The obtained mixture was stirred overnight at room temperature. The reaction mixture turned yellow and cloudy. 5 ml Water in 50 ml THF was added dropwise, followed by addition of 100 ml 5 M HCl. The resulting mixture was stirred for 15 minutes. 200 ml of brine was added and the resulting mixture was extracted three times with 200 ml dichloromethane. The organic layers were combined and successively dried and concentrated in vacuo to give 5.52 g of a dark red oil. Flash chromatographic purification (silica gel, gradient elution with petroleum ether (40-65)/diethylether=98/2→95/5 (v/v)) yielded (3.14 g) 7,7,7-trifluoro-2-methyl-hept-2-en-4-one. (Intermediate IIIb-2). $^1$H-NMR (400 MHz, CDCl$_3$) δ 1.91 (br s, 3H), 2.17 (br s, 3H), 2.36-2.48 (m, 2H), 2.68 (br t, J=7 Hz, 2H), 6.08 (br t, J=2, 1H).

Using analogous methods, intermediates IIIb-3 and IIIb-4 were synthesized:

Intermediate IIIb-3: 5-methyl-1-phenyl-hex-4-en-3-one: $^1$H-NMR (400 MHz, CDCl$_3$) δ 1.85 (br s, 3H), 2.14 (br s, 3H), 2.70 (t, J=7, 2H), 2.90 (t, J=7 Hz, 2H), 6.04 (br t, J=2, 1H), 7.12-7.18 (m, 3H), 7.21-7.27 (m, 2H).

Intermediate IIIb-4: 3-methyl-1-(2-phenyl-trans-cyclopropyl)but-2-en-1-one: $^1$H-NMR (400 MHz, CDCl$_3$) δ 1.29-1.36 (m, 1H), 1.66-1.72 (m, 1H), 1.88 (br s, 3H), 2.13-2.18 (m, 4H), 2.47-2.54 (m, 1H), 6.23 (br s, 1H), 7.08 (d, J=8, 2H), 7.14-7.19 (m, 1H), 7.22-7.28 (m, 2H).

To a magnetically stirred and ice-cooled solution of 2-methyl-oct-2-en-4-one (9.30 gram, 63 mmol) in dichloromethane (90 ml) was slowly added bromine (3.23 ml, 33 mmol; dissolved in 10 ml dichloromethane) and the resulting mixture was stirred for 10 minutes. To the obtained mixture was slowly added triethylamine (13.10 ml, 94.5 mmol: dissolved in 25 ml dichloromethane). The resulting mixture was allowed to attain room temperature and stirred for 1 hour and subsequently stirred for 16 hours at 40° C. The obtained mixture was washed with 1N HCl (100 ml), dried over MgSO$_4$, filtered and concentrated in vacuo to give crude 3-bromo-2-methyl-oct-2-en-4-one. Sepacore (40×300 mm column) separation (Gradient: first eluant: petroleum ether (40-60); second eluant: petroleum ether (40-60)/diethyl ether=98/2 (v/v)); third eluant: petroleum ether (40-60)/diethyl ether=95/5 (v/v)) gave 3-bromo-2-methyl-oct-2-en-4-one (Intermediate IIIc-1) pale-yellow oil (11.80 gram, 77% yield). $^1$H-NMR (400 MHz, CDCl$_3$) δ 0.92 (t, J=7.2 Hz, 3H), 1.29-1.39 (m, 2H), 1.56-1.66 (m, 2H), 2.00 (br s, 6H), 2.78 (t, J=7.4 Hz, 2H).

Using analogous methods, intermediates IIIc-2, IIIc-3 and IIIc-4 were synthesized:

Intermediate IIIc-2: 7,7,7-trifluoro-3-bromo-2-methyl-hept-2-en-4-one: $^1$H-NMR (400 MHz, CDCl$_3$) δ 2.04 (s, 3H), 2.08 (s, 3H), 2.38-2.50 (m, 2H), 3.09 (t, J=7 Hz, 2H).

Intermediate IIIc-3: 4-bromo-5-methyl-1-phenyl-hex-4-en-3-one: $^1$H-NMR (400 MHz, CDCl$_3$) δ 1.97 (s, 3H), 1.99 (s, 3H), 2.91-2.98 (m, 2H), 3.10-3.14 (m, 2H), 7.16-7.31 (m, 5H).

Intermediate IIIc-4: 2-bromo-3-methyl-1-(2-phenyl-trans-cyclopropyl)but-2-en-1-one: $^1$H-NMR (400 MHz, CDCl$_3$) δ 1.43-1.50 (m, 1H), 1.75-1.81 (m, 1H), 2.00 (s, 3H), 2.01 (s, 3H), 2.56-2.63 (m, 1H), 2.66-2.73 (m, 1H), 7.13-7.32 (m, 5H).

Intermediates IIIc-1, IIIc-2, IIIc-3 and IIIc-4

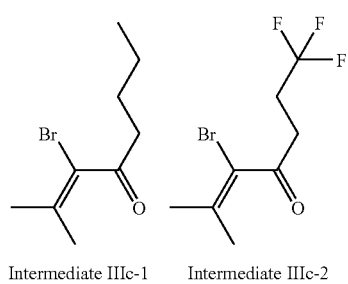

Intermediate IIIc-1    Intermediate IIIc-2

Intermediate IV-1

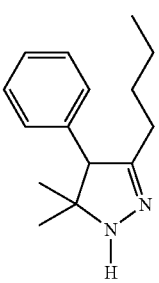

Intermediate IV-1

To a magnetically stirred solution of 2-methyl-3-phenyloct-2-en-4-one (Intermediate III-1) (1.96 gram, 9.07 mmol) in absolute ethanol (15 ml) was added hydrazine.hydrate (0.88 ml, 18.14 mmol) and the resulting solution was heated at reflux temperature for 4 hours under a nitrogen atmosphere. The resulting solution was allowed to attain room temperature, concentrated and taken up in a mixture of MTBE and water. The organic layer was collected, dried over $MgSO_4$, filtered and concentrated to give crude 3-(n-butyl)-5,5-dimethyl-4-phenyl-4,5-dihydropyrazole (Intermediate IV-1) (2.06 gram) as an oil. $^1$H-NMR (400 MHz, $CDCl_3$) δ 0.80-0.89 (m, 6H), 1.23-1.37 (m, 5H), 1.42-1.54 (m, 2H), 2.06-2.35 (m, 2H), 3.52 (s, 1H), 4.90 (br s, 1H), 7.07 (br d, J~8 Hz, 2H), 7.19-7.38 (m, 3H).

Intermediates VII-1 and VII-2

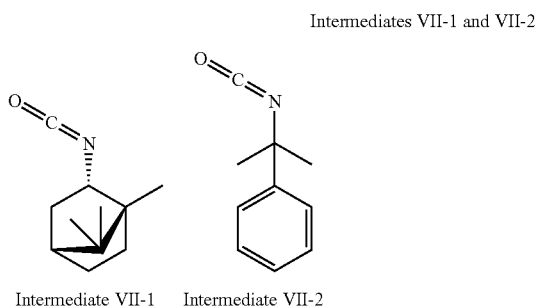

Intermediate VII-1    Intermediate VII-2

To a magnetically stirred solution of diphosgene (4.26 ml, 0.0353 mol) in dichloromethane (90 ml) was slowly added a solution of endo-(1R,2S,4R—)-1,7,7-trimethylbicyclo[2.2.1]hept-2-ylamine (CAS 32511-34-5) and N,N-dimethylaniline (15.2 ml, 0.12 mol)) in dichloromethane (90 ml) at 0° C. The resulting mixture was allowed to attain room temperature and stirred for 30 minutes. The mixture was concentrated and the residue taken up in dichloromethane, washed (3× with 1N HCl and 1× brine), dried ($MgSO_4$), filtered and concentrated in vacuo to give endo-2-isocyanato-[(1R,2S,4R)-1,7,7-trimethylbicyclo[2.2.1]heptane (10.43 g, 97% yield. $^1$H-NMR (400 MHz, $CDCl_3$) δ 0.85 (s, 3H), 0.86 (s, 3H), 0.89 (s, 3H), 1.11 (dd, J=13.2 and 4.2, 1H), 1.21-1.28 (m, 1H), 1.30-1.38 (m, 1H), 1.67 (t, J=4, 1H), 1.71-1.83 (m, 2H), 2.26-2.34 (m, 1H), 3.75 (ddd, J=10.5, 4.1 and 2.3, 1H). Optical rotation $([\alpha]_D)$=+40.2 (c=1.07, dichloromethane).

Intermediate VII-2 was prepared from diphosgene, cumylamine and N,N-dimethylaniline in dichloromethane analogously to the procedure described for intermediate VII-1. $^1$H-NMR (400 MHz, $CDCl_3$) δ 1.71 (s, 6H), 7.22-7.29 (m, 1H), 7.32-7.38 (m, 2H), 7.42-7.46 (m, 2H).

3-(n-Butyl)-5,5-dimethyl-4-phenyl-4,5-dihydro-(1H)-pyrazole-1-carbonyl chloride:

Intermediate VIII-1

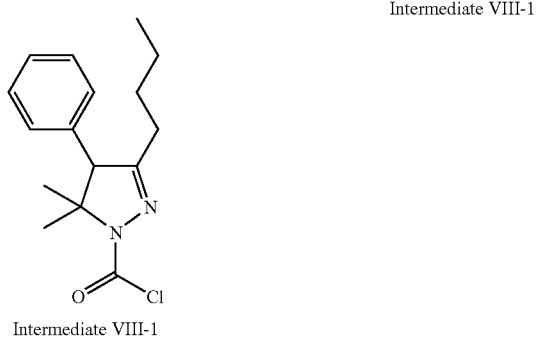 [SMILES: CCCCC1=NN(C(=O)Cl)C(C)(C)C1c1ccccc1]

Intermediate VIII-1

To a magnetically stirred solution of 3-(n-butyl)-5,5-dimethyl-4-phenyl-4,5-dihydropyrazole (Intermediate (IV-1) (0.47 gram, 1.43 mmol) in dichloromethane (10 ml) was successively added DIPEA (0.35 ml, 2.07 mmol) and trichloromethyl chloroformate (0.25 ml, 2.07 mmol, dissolved in 10 ml dichloromethane) at 0° C. and the resulting solution was allowed to attain room temperature and subsequently reacted at room temperature for 1 hour in a nitrogen atmosphere. Subsequent Sepacore column chromatographic purification (eluant: petroleum ether/diethyl ether=93/7 (v/v)) gave pure 3-(n-butyl)-5,5-dimethyl-4-phenyl-4,5-dihydro-(1H)-pyrazole-1-carbonyl chloride (Intermediate VIII-1) (0.20 g, 43% yield). (Intermediate VIII-1). $^1$H-NMR (400 MHz, $CDCl_3$) δ 0.87 (t, J=7, 3H), 1.11 (s, 3H), 1.27-1.39 (m, 2H), 1.45-1.59 (m, 5H), 2.10-2.20 (m, 1H), 2.36-2.46 (m, 1H), 3.91 (s, 1H), 7.01 (br d, J~8 Hz, 2H), 7.30-7.40 (m, 3H).

Example 4

Synthesis of Specific Compounds of the Invention

The specific compounds of which the synthesis is described below are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

Compound 1

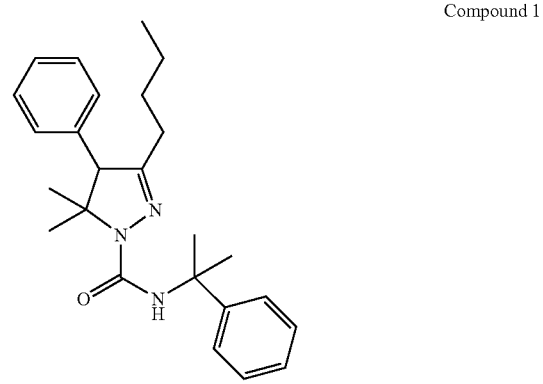 [SMILES: CCCCC1=NN(C(=O)NC(C)(C)c2ccccc2)C(C)(C)C1c1ccccc1]

N-(1-methyl-1-phenyl-ethyl)-3-(n-butyl)-5,5-dimethyl-4-phenyl-4,5-dihydro-(1H)-pyrazole-1-carboxamide Crude 3-(n-Butyl)-5,5-dimethyl-4-phenyl-4,5-dihydropyrazole (Intermediate IV-1) (1.03 gram, 4.48 mmol maximally) was dissolved in toluene (10 ml) and treated with 1-methyl-1-phenyl-ethylisocyanate (Intermediate VII-2) (0.72 g, 4.48 mmol) and 2 drops of triethylamine and the resulting solution was stirred at room temperature for 16 hours. The solution was concentrated and purified using Sepacore equipment: (petroleum ether/diethyl ether=85/15 (v/v)) to give N-(1-methyl-1-phenyl-ethyl)-3-(n-butyl)-5,5-dimethyl-4-phenyl-4,5-dihydro-(1H)-pyrazole-1-carboxamide as a colorless oil (0.97 gram, 55% yield). $R_f$(petroleum ether/diethyl ether=4/1 (v/v))~0.3. $^1$H-NMR (400 MHz, $CDCl_3$) δ 0.88 (t, J=7, 3H), 1.08 (s, 3H), 1.26-1.39 (m, 2H), 1.44 (s, 3H), 1.45-1.56 (m, 2H), 1.70 (s, 3H), 1.76 (s, 3H), 2.09-2.18 (m, 1H), 2.25-2.35 (m, 1H), 3.70 (s, 1H), 6.59 (br s, 1H), 7.03 (br d, J~8 Hz, 2H), 7.20 (br t, J~8 Hz, 1H), 7.26-7.36 (m, 5H), 7.44 (br d, J~8 Hz, 2H).

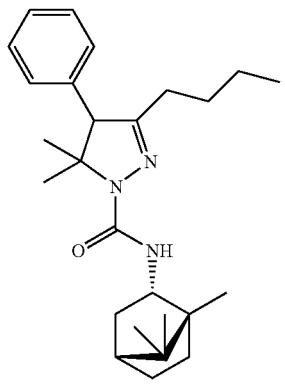

Compound 2

N-[Endo-(1R,2S,4R)-1,7,7-trimethylbicyclo[2.2.1]hept-2-yl]-3-(n-butyl)-5,5-dimethyl-4-phenyl-4,5-dihydro-(1H)-pyrazole-1-carboxamide (equimolar mixture of diastereoisomers)

Compound 2 was obtained from 3-(n-butyl)-5,5-dimethyl-4-phenyl-4,5-dihydropyrazole (Intermediate IV-1) and intermediate VII-1, analogously to the procedure described for compound 1. $^1$H-NMR (400 MHz, CDCl$_3$) Characteristic signals: δ 0.97 (s, 3H) (bornyl-CH$_3$ group), 1.11/1.14 and 1.48/1.51 (diastereotopic pyrazoline C$_5$—CH$_3$ groups), 3.70 and 3.73 (pyrazoline C$_4$—H proton). R$_f$ (petroleum ether 40-60/diethyl ether=4/1 (v/v))=0.3.

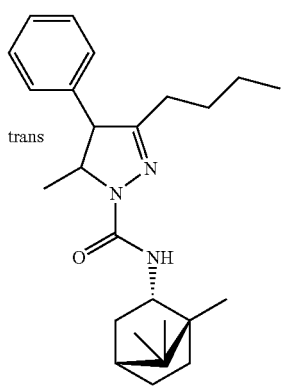

Compound 3

N-[Endo-(1R,2S,4R)-1,7,7-trimethylbicyclo[2.2.1]hept-2-yl]-3-(n-butyl)-5-methyl-4-phenyl-4,5-dihydro-3,4-trans-(1H)-pyrazole-1-carboxamide (equimolar mixture of diastereoisomers)

Compound 3 was obtained from 3-(n-butyl)-5-methyl-4-phenyl-4,5-dihydropyrazole and intermediate VII-1. Sepacore chromatographic separation (petroleum ether/diethyl ether=80/20 (v/v)) gave pure trans product (compound 3) and a fraction which consisted of a mixture of cis- and trans-product. $^1$H-NMR (400 MHz, CDCl$_3$); Compound 3: Characteristic signals: δ 0.96 (s, 3H) (bornyl-CH$_3$ group), 3.60 (br d, J~6, 1H) (pyrazoline C$_4$—H proton), 4.22-4.29 (m, 1H) (pyrazoline C$_5$—H proton). N.B.: This pyrazoline C$_5$—H proton is shifted to δ 4.39-4.48 in the corresponding cis compound. R$_f$ (petroleum ether 40-60/diethyl ether=4/1 (v/v))=0.3.

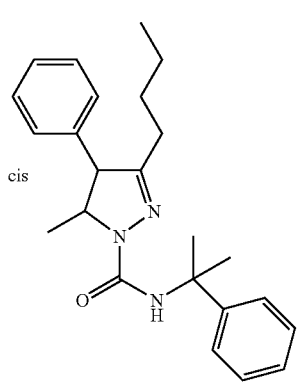

Compound 4

N-(1-methyl-1-phenyl-ethyl)-3-(n-butyl)-5-methyl-4-phenyl-4,5-cis-4,5-dihydro-(1H)-pyrazole-1-carboxamide Prepared from 3-(n-butyl)-5-methyl-4-phenyl-4,5-dihydropyrazole and 1-methyl-1-phenyl-ethylisocyanate (Intermediate VII-2) analogously to the procedure described for compound 1. The obtained crude mixture of N-(1-methyl-1-phenyl-ethyl)-3-(n-butyl)-5-methyl-4-phenyl-4,5-cis-4,5-dihydro-(1H)-pyrazole-1-carboxamide (compound 4) and N-(1-methyl-1-phenyl-ethyl)-3-(n-butyl)-5-methyl-4-phenyl-4,5-trans-4,5-dihydro-(1H)-pyrazole-1-carboxamide (compound 5) was separated by Sepacore chromatographic purification: (petroleum ether/diethyl ether=80/20 (v/v)) into pure compound 4 and pure compound 5. The 4,5-cis-trans assignment was based on NMR-NOE experiments, wherein the interaction between 4-phenyl ortho protons and the protons of the 5-methyl group was studied. Compound 4: $^1$H-NMR (400 MHz, CDCl$_3$) δ 0.87 (t, J=7, 3H), 0.97 (d, J=7, 3H), 1.24-1.39 (m, 2H), 1.42-1.55 (m, 2H), 1.73 (s, 3H), 1.76 (s, 3H), 2.06-2.15 (m, 1H), 2.23-2.32 (m, 1H), 4.22 (d, J=12, 1H), 4.36-4.46 (m, 1H), 6.46 (br s, 1H), 7.05 (br d, J~8 Hz, 2H), 7.18-7.37 (m, 6H), 7.46 (br d, J~8 Hz, 2H).

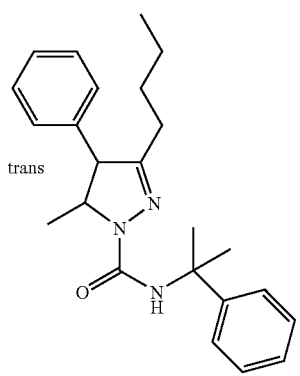

Compound 5

N-(1-methyl-1-phenyl-ethyl)-3-(n-butyl)-5-methyl-4-phenyl-4,5-trans-4,5-dihydro-(1H)-pyrazole-1-carboxamide ¹H-NMR (400 MHz, CDCl₃) δ 0.87 (t, J=7, 3H), 1.24-1.35 (m, 2H), 1.38 (d, J~6 Hz, 3H), 1.42-1.55 (m, 2H), 1.76 (s, 6H), 2.02-2.12 (m, 1H), 2.15-2.25 (m, 1H), 3.59 (d, J=6, 1H), 4.23 (quintet, J=6, 1H), 6.39 (br s, 1H), 7.10 (br d, J~8 Hz, 2H), 7.19-7.29 (m, 2H), 7.30-7.37 (m, 4H), 7.47 (br d, J~8 Hz, 2H).

Compound 6

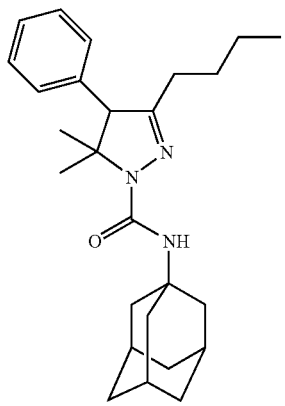

N-Adamantyl-3-(n-butyl)-5,5-dimethyl-4-phenyl-4,5-dihydro-(1H)-pyrazole-1-carboxamide Compound 6 was obtained from 3-(n-butyl)-5,5-dimethyl-4-phenyl-4,5-dihydropyrazole-1-carbonyl chloride (Intermediate VIII-1) and adamantylamine in dichloromethane (16 hours, room temperature). ¹H-NMR (400 MHz, CDCl₃) δ 0.87 (t, J=7.2 Hz, 3H) 1.13 (s, 3H) 1.24-1.36 (m, 2H) 1.41-1.54 (m, 5H) 1.63-1.76 (m, 6H) 2.04-2.14 (m, 10H) 2.21-2.31 (m, 1H) 3.67 (s, 1H) 6.00 (s, 1H) 6.98-7.04 (m, 2H) 7.25-7.35 (m, 3H).

Compound 7

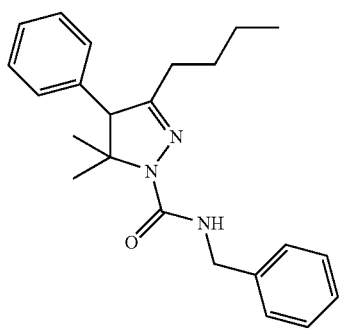

N-Benzyl-3-(n-butyl)-5,5-dimethyl-4-phenyl-4,5-dihydro-(1H)-pyrazole-1-carboxamide Compound 7 was obtained from 3-(n-butyl)-5,5-dimethyl-4-phenyl-4,5-dihydropyrazole (Intermediate IV-1) and benzylisocyanate. ¹H-NMR (400 MHz, CDCl₃) δ 0.85 (t, J=7.4 Hz, 3H) 1.17 (s, 3H) 1.21-1.35 (m, 2H) 1.38-1.51 (m, 2H) 1.53 (s, 3H) 2.05-2.14 (m, 1H) 2.20-2.29 (m, 1H) 3.73 (s, 1H) 4.49 (d, J=6.0 Hz, 2H) 6.42 (br t, J=5.7 Hz, 1H) 7.01 (d, J=6.6 Hz, 2H) 7.24-7.38 (m, 8H).

Analogously the compounds 8-38 were prepared.

Compound 8

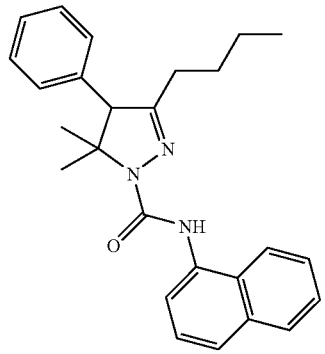

N-Naphtyl-3-(n-butyl)-5,5-dimethyl-4-phenyl-4,5-dihydro-(1H)-pyrazole-1-carboxamide ¹H-NMR (400 MHz, CDCl₃) δ 0.94 (t, J=7.2 Hz, 3H) 1.24 (s, 3H) 1.35-1.48 (m, 2H) 1.56-1.67 (m, 5H) 2.18-2.27 (m, 1H) 2.35-2.45 (m, 1H) 3.84 (s, 1H) 7.08 (d, J=6.9 Hz, 2H) 7.29-7.41 (m, 3H) 7.44-7.62 (m, 4H) 7.86 (d, J=7.5 Hz, 1H) 7.95 (d, J=8.4 Hz, 1H) 8.14 (d, J=7.5 Hz, 1H) 8.82 (s, 1H).

Compound 9

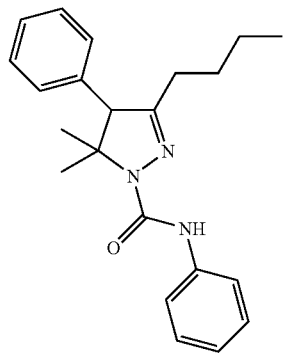

N-Phenyl-3-(n-butyl)-5,5-dimethyl-4-phenyl-4,5-dihydro-(1H)-pyrazole-1-carboxamide ¹H-NMR (400 MHz, CDCl₃) δ 0.90 (t, J=7.4 Hz, 3H) 1.20 (s, 3H) 1.25-1.42 (m, 2H) 1.46-1.58 (m, 2H) 1.57 (s, 3H) 2.10-2.21 (m, 1H) 2.28-2.38 (m, 1H) 3.78 (s, 1H) 6.98-7.05 (m, 3H) 7.25-7.38 (m, 5H) 7.52 (d, J=7.5 Hz, 2H) 8.18 (br s, 1H).

Compound 10

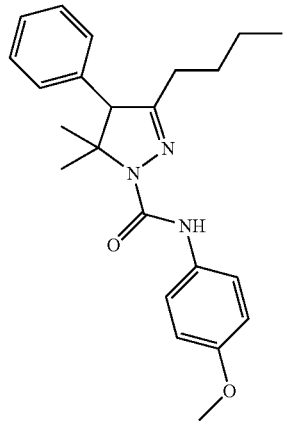

N-(4-Methoxyphenyl)-3-(n-butyl)-5,5-dimethyl-4-phenyl-4,5-dihydro-(1H)-pyrazole-1-carboxamide ¹H-NMR (400 MHz, CDCl₃) δ 0.89 (t, J=7.4 Hz, 3H) 1.19 (s, 3H) 1.28-1.40 (m, 2H) 1.48-1.59 (m, 5H) 2.10-2.20 (m, 1H) 2.27-2.37 (m, 1H) 3.78 (s, 4H) 6.83-6.87 (m, 2H) 7.01-7.05 (m, 2H) 7.27-7.37 (m, 3H) 7.39-7.44 (m, 2H) 8.02 (br s, 1H).

Compound 11

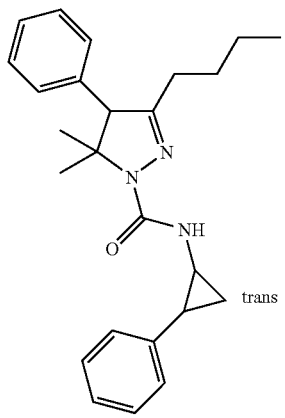

N-(2-Phenyl-trans-cyclopropyl)-3-(n-butyl)-5,5-dimethyl-4-phenyl-4,5-dihydro-(1H)-pyrazole-1-carboxamide ¹H-NMR (400 MHz, CDCl₃) δ 0.87 (double t, J=7.3 Hz, 3H) 1.16 (s, 3H) 1.18-1.38 (m, 4H) 1.40-1.56 (m, 5H) 2.06-2.15 (m, 2H) 2.22-2.31 (m, 1H) 2.88-2.93 (m, 1H) 3.71 (s, 1H) 6.34 (br s, 1H), 7.00 (d, J=6.6 Hz, 2H) 7.12-7.20 (m, 3H) 7.22-7.36 (m, 5H).

Compound 12

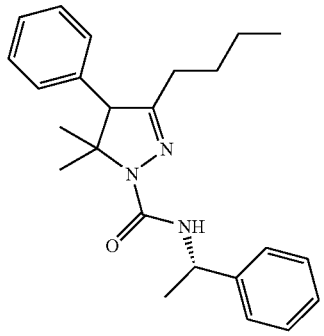

N—((S)-1-Phenyl-ethyl)-3-(n-butyl)-5,5-dimethyl-4-phenyl-4,5-dihydro-(1H)-pyrazole-1-carboxamide ¹H-NMR (400 MHz, CDCl₃) δ 0.87 (doublet, J=7.2 Hz, 3H) 1.11/1.15 (double s, 3H) 1.22-1.38 (m, 2H) 1.41-1.57 (m, 8H) 2.06-2.15 (m, 1H) 2.23-2.33 (m, 1H) 3.70/3.72 (double s, 1H) 5.00-5.10 (m, 1H) 6.35-6.42 (m, 1H) 6.98-7.05 (m, 2H) 7.20-7.43 (m, 8H).

Compound 13

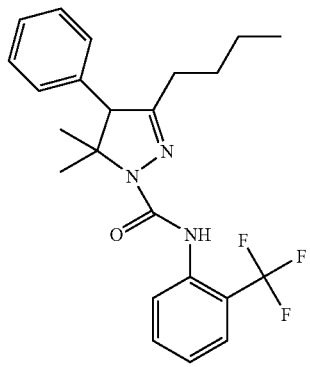

N-(2-(Trifluoromethyl)phenyl)-3-(n-butyl)-5,5-dimethyl-4-phenyl-4,5-dihydro-(1H)-pyrazole-1-carboxamide ¹H-NMR (400 MHz, CDCl₃) δ 0.90 (t, J=7.4 Hz, 3H) 1.20 (s, 3H) 1.28-1.45 (m, 2H) 1.55-1.64 (m, 5H) 2.12-2.21 (m, 1H) 2.25-2.35 (m, 1H) 3.81 (s, 1H) 7.04 (d, J=6.6 Hz, 2H) 7.08 (t, J=7.7 Hz, 1H) 7.28-7.38 (m, 3H) 7.50 (t, J=7.8 Hz, 1H) 7.57 (d, J=7.8 Hz, 1H) 8.36 (d, J=8.4 Hz, 1H) 8.90 (br s, 1H).

Compound 14

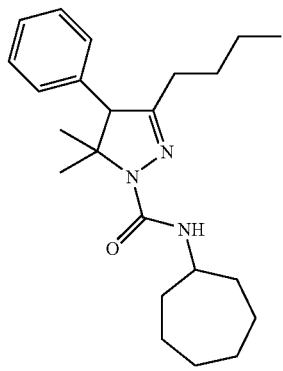

N-Cycloheptyl-3-(n-butyl)-5,5-dimethyl-4-phenyl-4,5-dihydro-(1H)-pyrazole-1-carboxamide ¹H-NMR (400 MHz, CDCl₃) δ 0.87 (t, J=7.2 Hz, 3H) 1.13 (s, 3H) 1.23-1.37 (m, 2H) 1.42-1.71 (m, 15H) 1.94-2.03 (m, 2H) 2.06-2.15 (m, 1H) 2.22-2.32 (m, 1H) 3.70 (s, 1H) 3.80-3.90 (m, 1H) 6.04 (br d, J=8 Hz, 1H) 7.01 (d, J=6.3 Hz, 2H) 7.25-7.36 (m, 3H).

Compound 15

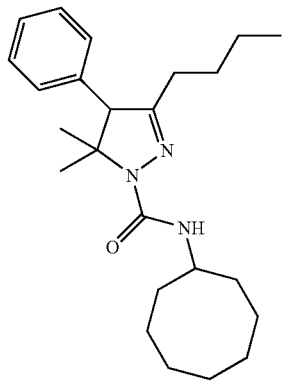

N-Cyclooctyl-3-(n-butyl)-5,5-dimethyl-4-phenyl-4,5-dihydro-(1H)-pyrazole-1-carboxamide $^1$H-NMR (400 MHz, CDCl$_3$) δ 0.87 (t, J=7.2 Hz, 3H) 1.13 (s, 3H) 1.23-1.38 (m, 2H) 1.39-1.75 (m, 17H) 1.84-1.96 (m, 2H) 2.04-2.14 (m, 1H) 2.22-2.32 (m, 1H) 3.69 (s, 1H) 3.84-3.95 (m, 1H) 6.05 (br d, J=8.1 Hz, 1H) 7.01 (d, J=6.6 Hz, 2H) 7.25-7.36 (m, 3H).

Compound 16

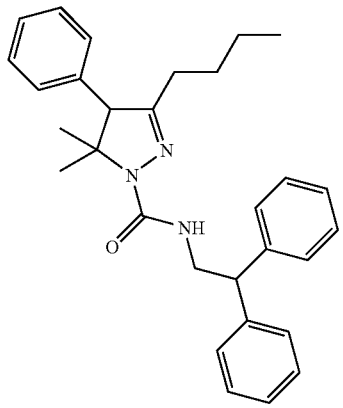

N-(2,2-Diphenylethyl)-3-(n-butyl)-5,5-dimethyl-4-phenyl-4,5-dihydro-(1H)-pyrazole-1-carboxamide $^1$H-NMR (400 MHz, CDCl$_3$) δ 0.84 (t, J=7.4 Hz, 3H) 1.11 (s, 3H) 1.14-1.30 (m, 2H) 1.31-1.44 (m, 2H) 1.45 (s, 3H) 1.97-2.05 (m, 1H) 2.08-2.18 (m, 1H) 3.64 (s, 1H) 3.83-3.99 (m, 2H) 4.26 (t, J=7.8 Hz, 1H) 6.10 (br t, J=5.9 Hz, 1H) 6.95 (d, J=6.6 Hz, 2H) 7.18-7.34 (m, 13H).

Compound 17

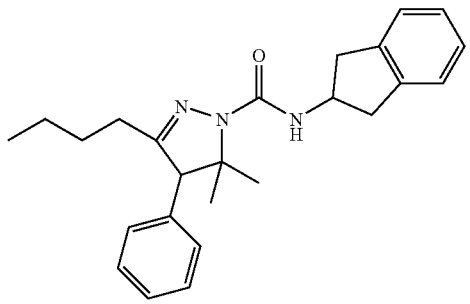

N-(2-Indanyl)-3-(n-butyl)-5,5-dimethyl-4-phenyl-4,5-dihydro-(1H)-pyrazole-1-carboxamide $^1$H-NMR (400 MHz, CDCl$_3$) δ 0.84 (t, J=7.2 Hz, 3H) 1.15 (s, 3H) 1.21-1.34 (m, 2H) 1.37-1.50 (m, 2H) 1.51 (s, 3H) 2.03-2.12 (m, 1H) 2.20-2.29 (m, 1H) 2.85-2.94 (m, 2H) 3.32-3.41 (m, 2H) 3.70 (s, 1H) 4.63-4.73 (m, 1H) 6.26 (br d, J=7.8 Hz, 1H) 7.00 (d, J=6.3 Hz, 2H) 7.15-7.21 (m, 2H) 7.21-7.27 (m, 2H) 7.28-7.37 (m, 3H).

Compound 18

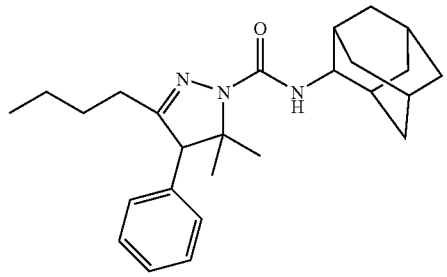

N-(2-adamantyl)-3-(n-butyl)-5,5-dimethyl-4-phenyl-4,5-dihydro-(1H)-pyrazole-1-carboxamide $^1$H-NMR (400 MHz, CDCl$_3$) δ 0.83 (t, J=7.3 Hz, 3H) 1.22 (s, 6H) 1.23-1.30 (m, 2H) 1.38-1.98 (m, 16H) 1.99-3.06 (m, 2H) 3.92-3.99 (m, 1H) 4.28 (br s, 1H) 7.07-7.15 (m, 3H) 7.27-7.37 (m, 3H).

Compound 19

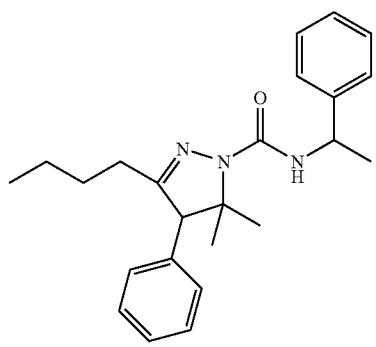

rel, exo

N-(rel-exo-bicyclo[2.2.1]hept-2-yl)-3-(n-butyl)-5,5-dimethyl-4-phenyl-4,5-dihydro-(1H)-pyrazole-1-carboxamide $^1$H-NMR (400 MHz, CDCl$_3$) δ 0.87 (t, J=7.4 Hz, 3H) 1.13 (d, J=3.6 Hz, 3H) 1.15-1.37 (m, 6H) 1.38-1.58 (m, 8H) 1.76-1.85 (m, 1H) 2.04-2.15 (m, 1H) 2.21-2.32 (m, 3H) 3.62-3.69 (m, 1H) 3.69 (s, 1H) 5.92 (br d, J=6.0 Hz, 1H) 6.98-7.03 (m, 2H) 7.27-7.36 (m, 3H).

Compound 20

N-(1-phenyl-ethyl)-5,5-dimethyl-4-phenyl-4,5-dihydro-(1H)-pyrazole-1-carboxamide $^1$H-NMR (400 MHz, CDCl$_3$) δ 0.84-0.91 (m, 3H) 1.10/1.14 (double s, Signals together integrate for 3H) 1.21-1.56 (m, 10H) 2.06-2.15 (m, 1H) 2.23-2.33 (m, 1H) 3.71 (double s, Signals together integrate for 1H) 4.99-5.09 (m, 1H) 6.33-6.40 (m, 1H) 6.97-7.05 (m, 2H) 7.20-7.42 (m, 8H).

Compound 21

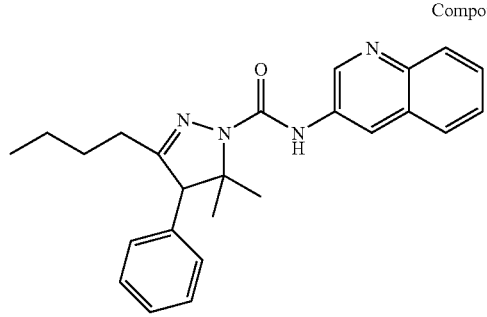

N-(Quinolin-3-yl)-5,5-dimethyl-4-phenyl-4,5-dihydro-(1H)-pyrazole-1-carboxamide $^1$H-NMR (400 MHz, CDCl$_3$) δ 0.92 (t, J=7.4 Hz, 3H) 1.24 (s, 3H) 1.30-1.44 (m, 2H) 1.49-1.63 (m, 5H) 2.15-2.24 (m, 1H) 2.34-2.44 (m, 1H) 3.84 (s, 1H) 7.05 (d, J=6.6 Hz, 2H) 7.30-7.41 (m, 3H) 7.46-7.53 (m, 1H) 7.58 (dt, J=7.7, 1.5 Hz, 1H) 7.76-7.80 (m, 1H) 8.03 (d, J=8.4 Hz, 1H) 8.42 (s, 1H) 8.73 (q, J=2.6 Hz, 2H).

Compound 22

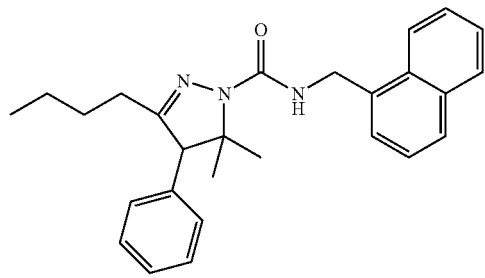

N-(Naphtalen-1-ylmethyl)-5,5-dimethyl-4-phenyl-4,5-dihydro-(1H)-pyrazole-1-carboxamide $^1$H-NMR (400 MHz, CDCl$_3$) δ 0.81 (t, J=7.2 Hz, 3H) 1.19 (s, 3H) 1.21-1.32 (m, 2H) 1.34-1.48 (m, 2H) 1.55 (s, 3H) 2.00-2.12 (m, 1H) 2.15-2.24 (m, 1H) 3.72 (s, 1H) 4.95 (dd, J=5.6, 2.86 Hz, 2H) 6.40 (br t, J=5.6 Hz, 1H) 6.98-7.02 (m, 2H) 7.27-7.36 (m, 3H) 7.38-7.59 (m, 4H) 7.81 (d, J=8.1 Hz, 1H) 7.86-7.91 (m, 1H) 8.16 (d, J=8.4 Hz, 1H).

Compound 23

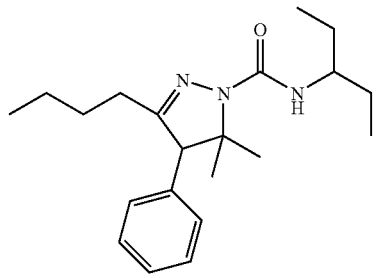

N-[1-(ethyl)propyl]-5,5-dimethyl-4-phenyl-4,5-dihydro-(1H)-pyrazole-1-carboxamide $^1$H-NMR (400 MHz, CDCl$_3$) δ 0.87 (t, J=7.4 Hz, 3H) 0.91-0.98 (m, 6H) 1.14 (s, 3H) 1.22-1.61 (m, 11H) 2.06-2.15 (m, 1H) 2.23-2.33 (m, 1H) 3.59-3.69 (m, 1H) 3.70 (s, 1H) 5.88 (br d, J=9.0 Hz, 1H) 7.00-7.04 (m, 2H) 7.27-7.36 (m, 3H).

Compound 24

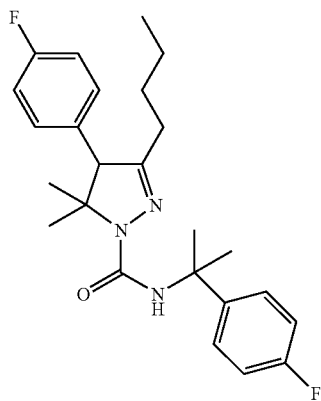

N-(1-Methyl-1-(4-fluorophenyl)-ethyl)-3-(n-butyl)-5,5-dimethyl-4-(4-fluorophenyl)-4,5-dihydro-(1H)-pyrazole-1-carboxamide $^1$H-NMR (400 MHz, CDCl$_3$) δ 0.88 (t, J=7, 3H), 1.08 (s, 3H), 1.23-1.39 (m, 2H), 1.42 (s, 3H), 1.43-1.55 (m, 2H), 1.67 (s, 3H), 1.74 (s, 3H), 2.07-2.16 (m, 1H), 2.25-2.35 (m, 1H), 3.68 (s, 1H), 6.56 (br s, 1H), 6.95-7.05 (m, 6H), 7.36-7.41 (m, 2H).

Compound 25

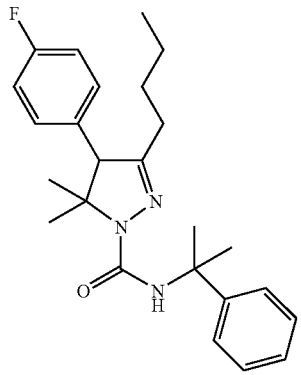

N-(1-Methyl-1-phenyl-ethyl)-3-(n-butyl)-5,5-dimethyl-4-(4-fluorophenyl)-4,5-dihydro-(1H)-pyrazole-1-carboxamide $^1$H-NMR (400 MHz, CDCl$_3$) δ 0.88 (t, J=7, 3H), 1.09 (s, 3H), 1.23-1.39 (m, 2H), 1.41-1.55 (m, 5H), 1.70 (s, 3H), 1.77 (s, 3H), 2.07-2.15 (m, 1H), 2.26-2.34 (m, 1H), 3.67 (s, 1H), 6.58 (br s, 1H), 6.95-7.05 (m, 4H), 7.17-7.22 (m, 1H), 7.29-7.34 (m, 2H), 7.41-7.46 (m, 2H).

Compound 26

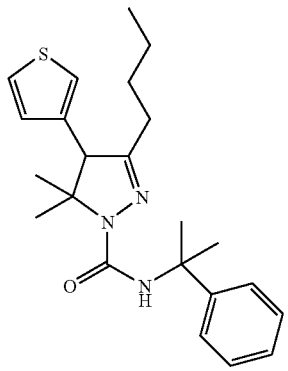

N-(1-Methyl-1-phenyl-ethyl)-3-(n-butyl)-5,5-dimethyl-4-(3-thienyl)-4,5-dihydro-(1H)-pyrazole-1-carboxamide $^1$H-NMR (400 MHz, DMSO-d$_6$) δ 0.84 (t, J=7, 3H), 0.97 (s, 3H), 1.22-1.34 (m, 2H), 1.36 (s, 3H), 1.39-1.52 (m, 2H), 1.61 (s, 3H), 1.64 (s, 3H), 2.10-2.19 (m, 1H), 2.23-2.33 (m, 1H), 4.08 (s, 1H), 6.60 (s, 1H), 6.87 (d, J=5 Hz, 1H), 7.17-7.21 (m, 1H), 7.27-7.40 (m, 5H), 7.54 (dd, J=5 and 3, 1H).

Compound 27

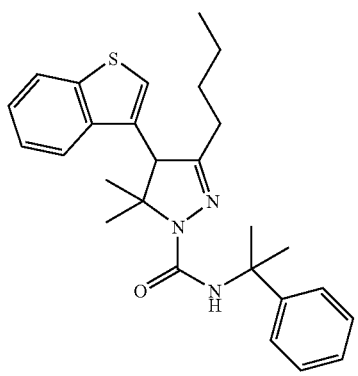

N-(1-Methyl-1-phenyl-ethyl)-3-(n-butyl)-5,5-dimethyl-4-(3-benzothienyl)-4,5-dihydro-(1H)-pyrazole-1-carboxamide $^1$H-NMR (400 MHz, CDCl$_3$): Some double peaks are present due to restricted amide bond rotations. δ 0.83-0.92 (m, 3H), 1.13 (s, 3H), 1.28-1.40 (m, 2H), 1.44-1.58 (m, 5H), 1.71, 1.77 and 1.79 (3×s, 6H), 2.17-2.28 (m, 1H), 2.34-2.44 (m, 1H), 4.25 (s, 1H), 6.58 and 6.63 (2×s, 1H), 7.02 (s, 1H), 7.18-7.23 (m, 2H), 7.30-7.50 (m, 5H), 7.62-7.72 (m, 1H), 7.81-7.92 (m, 1H).

Compound 28

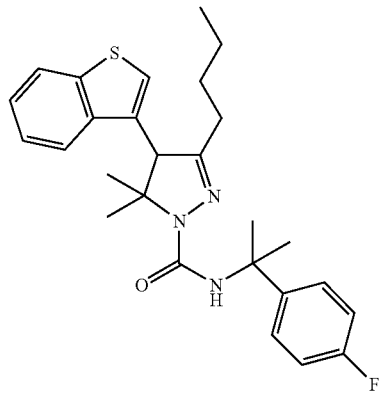

N-(1-Methyl-1-(4-fluorophenyl)-ethyl)-3-(n-butyl)-5,5-dimethyl-4-(3-benzothienyl)-4,5-dihydro-(1H)-pyrazole-1-carboxamide $^1$H-NMR (400 MHz, DMSO-d$_6$) (140° C.) δ 0.84 (t, J=7, 3H), 1.10 (s, 3H), 1.29-1.40 (m, 2H), 1.48-1.59 (m, 5H), 1.70 (s, 3H), 1.71 (s, 3H), 2.15-2.36 (m, 2H), 4.42 (s, 1H), 6.55 (s, 1H), 7.04-7.11 (m, 2H), 7.36-7.50 (m, 5H), 7.77-7.84 (m, 1H), 7.97 (br d, J=8, 1H).

Compound 29

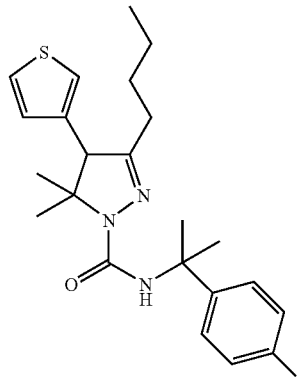

N-(1-Methyl-1-(4-fluorophenyl)-ethyl)-3-(n-butyl)-5,5-dimethyl-4-(3-thienyl)-4,5-dihydro-(1H)-pyrazole-1-carboxamide $^1$H-NMR (400 MHz, DMSO-d$_6$) δ 0.83 (t, J=7, 3H), 0.95 (s, 3H), 1.22-1.35 (m, 5H), 1.36-1.52 (m, 2H), 1.59 (s, 3H), 1.61 (s, 3H), 2.09-2.18 (m, 1H), 2.22-2.32 (m, 1H), 4.07 (s, 1H), 6.60 (s, 1H), 6.86 (dd, J=5 and 1.5 Hz, 1H), 7.06-7.14 (m, 2H), 7.31 (dd, J=3 and 1.2 Hz, 1H), 7.34-7.40 (m, 2H), 7.54 (dd, J=5 and 3, 1H).

Compound 30

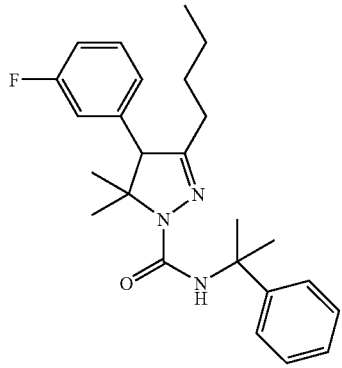

N-(1-Methyl-1-phenyl-ethyl)-3-(n-butyl)-5,5-dimethyl-4-(3-fluorophenyl)-4,5-dihydro-(1H)-pyrazole-1-carboxamide ¹H-NMR (400 MHz, CDCl₃) δ 0.90 (t, J=7, 3H), 1.11 (s, 3H), 1.26-1.39 (m, 2H), 1.43 (s, 3H), 1.44-1.55 (m, 2H), 1.71 (s, 3H), 1.76 (s, 3H), 2.08-2.18 (m, 1H), 2.26-2.36 (m, 1H), 3.67 (s, 1H), 6.57 (br s, 1H), 6.74 (br d, J=8, 1H), 6.82 (d, J=8, 1H), 6.98 (td, J=8 and 3, 1H), 7.17-7.22 (m, 1H), 7.27-7.36 (m, 3H), 7.43 (d, J=8, 2H).

Compound 31

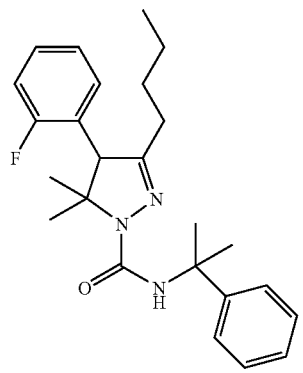

N-(1-Methyl-1-phenyl-ethyl)-3-(n-butyl)-5,5-dimethyl-4-(2-fluorophenyl)-4,5-dihydro-(1H)-pyrazole-1-carboxamide ¹H-NMR (400 MHz, CDCl₃) δ 0.90 (t, J=7, 3H), 1.15 (s, 3H), 1.29-1.39 (m, 2H), 1.43-1.57 (m, 5H), 1.70 (s, 3H), 1.76 (s, 3H), 2.08-2.17 (m, 1H), 2.27-2.37 (m, 1H), 4.18 (br s, 1H), 6.56 (br s, 1H), 6.88-7.35 (m, 7H), 7.43 (d, J=8, 2H).

Compound 32

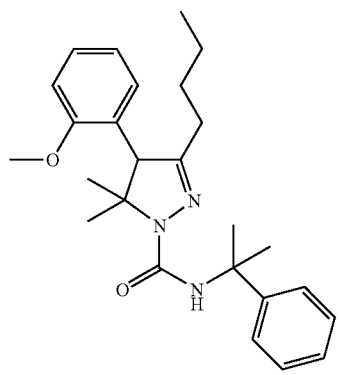

N-(1-Methyl-1-phenyl-ethyl)-3-(n-butyl)-5,5-dimethyl-4-(2-methoxyphenyl)-4,5-dihydro-(1H)-pyrazole-1-carboxamide ¹H-NMR (400 MHz, CDCl₃) δ 0.90 (t, J=7, 3H), 1.10 (s, 3H), 1.28-1.39 (m, 2H), 1.44 (s, 3H), 1.45-1.55 (m, 2H), 1.69 (s, 3H), 1.77 (s, 3H), 2.08-2.17 (m, 1H), 2.25-2.35 (m, 1H), 3.82 (s, 3H), 4.37 (s, 1H), 6.56 (br s, 1H), 6.78-6.82 (m, 1H), 6.87-6.94 (m, 2H), 7.17-7.36 (m, 4H), 7.43 (d, J=8, 2H).

Compound 33

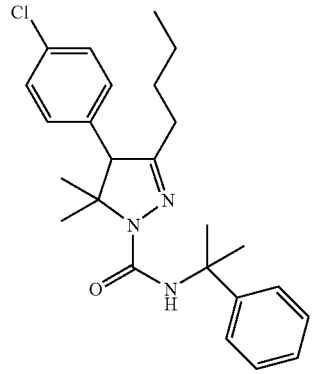

N-(1-Methyl-1-phenyl-ethyl)-3-(n-butyl)-5,5-dimethyl-4-(4-chlorophenyl)-4,5-dihydro-(1H)-pyrazole-1-carboxamide ¹H-NMR (400 MHz, CDCl₃) δ 0.89 (t, J=7, 3H), 1.09 (s, 3H), 1.25-1.38 (m, 2H), 1.42-1.57 (m, 5H), 1.70 (s, 3H), 1.76 (s, 3H), 2.04-2.15 (m, 1H), 2.23-2.34 (m, 1H), 3.66 (s, 1H), 6.56 (br s, 1H), 6.96 (d, J=8, 2H), 7.17-7.23 (m, 1H), 7.29-7.36 (m, 4H), 7.43 (d, J=8, 2H).

Compound 34

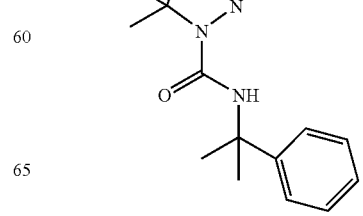

N-(1-Methyl-1-phenyl-ethyl)-3-(2-phenyl-trans-cyclopropyl)-5,5-dimethyl-4-phenyl-4,5-dihydro-(1H)-pyrazole-1-carboxamide (equimolar diastereomeric mixture)

¹H-NMR (400 MHz, CDCl₃) δ 1.09 and 1.11 (2×s, 3H), 1.13-1.38 (m, 2H), 1.47 (s, 3H), 1.55-1.62 and 2.11-2.18 (2×m, 1H), 1.69-1.77 and 2.31-2.38 (2×m, 7H), 3.72 (br s, 1H), 6.52 and 6.54 (2×br s, 1H), 6.88-6.94 (m, 2H), 7.05-7.37 (m, 11H), 7.43 (br d, J=8, 2H).

Compound 35

N-(1-Methyl-1-phenyl-ethyl)-3-(2-phenyl-ethyl)-5,5-dimethyl-4-phenyl-4,5-dihydro-(1H)-pyrazole-1-carboxamide ¹H-NMR (400 MHz, CDCl₃) δ 1.05 (s, 3H), 1.38 (s, 3H), 1.70 (s, 3H), 1.76 (s, 3H), 2.40-2.50 (m, 1H), 2.58-2.68 (m, 1H), 2.82-2.96 (m, 2H), 3.63 (s, 1H), 6.53 (br s, 1H), 6.96 (br d, J=8, 2H), 7.13-7.36 (m, 11H), 7.41 (br d, J=8, 2H).

Compound 36

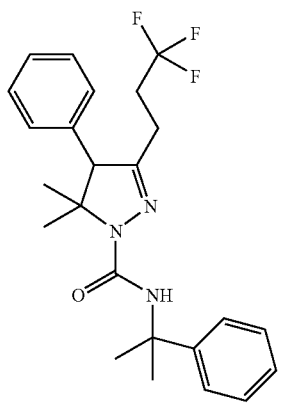

N-(1-Methyl-1-phenyl-ethyl)-3-(3,3,3-trifluoropropyl)-5,5-dimethyl-4-phenyl-4,5-dihydro-(1H)-pyrazole-1-carboxamide ¹H-NMR (400 MHz, CDCl₃) δ 1.10 (s, 3H), 1.47 (s, 3H), 1.71 (s, 3H), 1.76 (s, 3H), 2.37-2.55 (m, 4H), 3.71 (s, 1H), 6.48 (br s, 1H), 7.02 (br d, J=8, 2H), 7.17-7.23 (m, 1H), 7.28-7.38 (m, 5H), 7.43 (br d, J=8, 2H).

Compounds 37 and 38

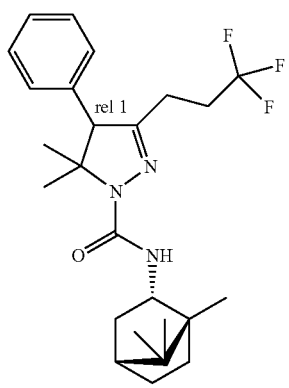

rel 1: relative configuration 1

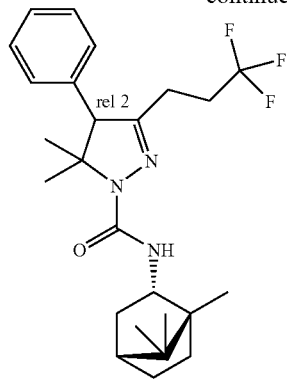

rel 2: relative configuration 2

N-[Endo-(1R,2S,4R)-1,7,7-trimethylbicyclo[2.2.1]hept-2-yl]-3-(3,3,3-trifluoropropyl)-5,5-dimethyl-4-phenyl-4,5-dihydro-(1H)-pyrazole-1-carboxamide (diastereoisomer 1) and N-[Endo-(1R,2S,4R)-1,7,7-trimethylbicyclo[2.2.1]hept-2-yl]-3-(3,3,3-trifluoropropyl)-5,5-dimethyl-4-phenyl-4,5-dihydro-(1H)-pyrazole-1-carboxamide (diastereoisomer 2)

Compounds 37 and 38 were separated by flash chromatography (silicagel, eluant gradient: petroleum ether (40-60)/diethyl ether=9/1 (v/v) to petroleum ether (40-60)/diethyl ether=8/2 (v/v).

Compound 37: Optical rotation ([α]$_D$)=+105 (c=1, MeOH, 25° C.). ¹H-NMR (400 MHz, CDCl₃) δ 0.83-1.00 (m, 10H), 1.13 (s, 3H), 1.21-1.62 (m, 7H), 1.68 (t, J~5, 1H), 1.74-1.87 (m, 1H), 2.35-2.60 (m, 4H), 3.76 (s, 1H), 4.10-4.20 (m, 1H), 6.14 (br d, J~9, 1H), 7.02 (br d, J~8, 2H), 7.28-7.41 (m, 3H).

Compound 38: Optical rotation ([α]$_D$)=-89 (c=1, MeOH, 25° C.). ¹H-NMR (400 MHz, CDCl₃) δ 0.83-0.98 (m, 10H), 1.15 (s, 3H), 1.21-1.60 (m, 7H), 1.68 (t, J~5, 1H), 1.74-1.87 (m, 1H), 2.35-2.60 (m, 4H), 3.72 (s, 1H), 4.12-4.21 (m, 1H), 6.13 (br d, J~9, 1H), 7.01 (br d, J~8, 2H), 7.28-7.41 (m, 3H).

Compound 39

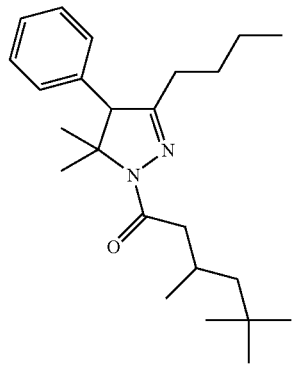

[3-(n-butyl)-5,5-dimethyl-4-phenyl-4,5-dihydro-(1H)-pyrazol-1-yl]-3,5,5-trimethylhexan-1-one (1:1 mixture of diastereomers)

To a magnetically stirred solution of 3-(n-butyl)-5,5-dimethyl-4-phenyl-4,5-dihydro-(1H)-pyrazole (1 ml: 0.25 M in anhydrous tetrahydrofuran, 0.25 mmol) was successively added 3,5,5-trimethylhexanoyl chloride (1.1 ml: 0.25 M in anhydrous tetrahydrofuran; 0.275 mmol) and DIPEA (1.1 ml: 0.285 M in anhydrous tetrahydrofuran; 0.313 mmol) and the resulting mixture was stirred for 21 hours at 30° C. An aqueous 5% NaHCO$_3$ solution and dichloromethane were added to the mixture. The organic layer was separated, successively washed with brine and water, dried over MgSO$_4$, filtered and concentrated in vacuo to give [3-(n-butyl)-5,5-dimethyl-4-phenyl-4,5-dihydro-(1H)-pyrazol-1-yl]-3,5,5-trimethyl-hexan-1-one as a mixture of diastereomers (55 mg, 57% yield). $^1$H-NMR (400 MHz, CDCl$_3$) δ 0.88 (t, J=7, 3H), 0.94 (s, 9H), 1.00 and 1.01 (2×d, J=7, 3H), 1.12-1.20 (m, 4H), 1.25-1.39 (m, 3H), 1.47-1.58 (m, 5H), 2.07-2.34 (m, 3H), 2.46-2.55 (m, 1H), 2.63-2.73 (m, 1H), 3.72 and 3.74 (2×s, 1H), 6.98 (br d, J=8 Hz, 2H), 7.28-7.37 (m, 3H).

Example 5

Formulations Used in Animal Studies

For oral (p.o.) administration: to the desired quantity (0.5-5 mg) of the solid compound 1 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 6

Pharmacological Methods

In vitro affinity for cannabinoid-CB$_1$ receptors was determined using membrane preparations of CHO cells in which human cannabinoid CB$_1$ receptors were stably transfected in conjunction with [$^3$H]CP-55,940 as radioligand. After incubation of a freshly prepared cell membrane preparation with the [$^3$H]-ligand, with or without addition of compounds of the invention, separation of bound and free ligand was performed by filtration over glassfiber filters. Radioactivity on the filter was measured by liquid scintillation counting.

In vitro affinity for cannabinoid-CB$_2$ receptors: was determined using membrane preparations of CHO cells in which human cannabinoid CB$_2$ receptors were stably transfected in conjunction with [$^3$H]CP-55,940 as radioligand. After incubation of a freshly prepared cell membrane preparation with the [$^3$H]-ligand, with or without addition of compounds of the invention, separation of bound and free ligand was performed by filtration over glassfiber filters. Radioactivity on the filter was measured by liquid scintillation counting.

In vitro cannabinoid-CB$_1$ receptor (ant)agonism was assessed with human CB$_1$ receptors cloned in CHO cells. CHO cells were grown in a DMEM culture medium, supplemented with 10% heat-inactivated fetal calf serum. Medium was aspirated and replaced by DMEM, without fetal calf serum, but containing [$^3$H]-arachidonic acid and incubated overnight in a cell culture stove (5% CO$_2$/95% air; 37° C.; water-saturated atmosphere). During this period [$^3$H]-arachidonic acid was incorporated in membrane phospholipids. On the test day, medium was aspirated and cells were washed three times using 0.5 ml DMEM, containing 0.2% BSA. CB$_1$ agonist stimulation lead to activation of PLA$_2$ followed by release of [$^3$H]-arachidonic acid into the medium. This CB$_1$ agonist-induced release was concentration-dependently antagonized by CB$_1$ receptor antagonists, such as rimonabant.

In vitro cannabinoid-CB$_2$ receptor (ant)agonism was assessed using a forskolin-stimulated cAMP accumulation assay. The ability of compounds to stimulate and inhibit adenylate cyclase activity was assessed in CHO K$_1$ cells expressing human CB$_2$ (Euroscreen, Brussels) receptor. CHO cells were grown in a CHO—S—SFM-II culture medium, supplemented with 10% heat-inactivated foetal calf serum, 2 mM glutamine, 400 µg/ml Hygromycine B and 500 µg/ml G418 at 37° C. in 93% air/5% CO$_2$. For incubation with test compounds, confluent cultures grown in 24 well plates were used. Each condition or substance was routinely tested in quadruplicate. Cells were loaded with 1 mCi [$^3$H]-adenine in 0.5 ml medium per well. After 2 hours, cultures were washed with 0.5 ml PBS containing 1 mM IBMX and incubated for 20 minutes with 0.5 ml PBS containing 1 mM IBMX and $3 \times 10^{-7}$ M forskolin with or without the test compound. Antagonistic effects of test compounds were determined as inhibition of 0.1 µM JWH-133-decreased [$^3$H]cAMP formation. After aspiration the reaction was stopped with 1 ml trichloroacetic acid (5% w/v). The [$^3$H]-ATP and [$^3$H]-cAMP formed in the cellular extract were assayed as follows: a volume of 0.8 ml of the extract was passed over Dowex (50WX-4200-400 mesh) and aluminum oxide columns, eluted with water and 0.1M imidazole (pH=7.5). Eluates were mixed with 7 ml Ultima-Flo [AP] and the β-radioactivity was counted with a liquid scintillation counter. The conversion of [$^3$H]-ATP into [$^3$H]-cAMP was expressed as the ratio in percentage radioactivity in the cAMP fraction as compared to the combined radioactivity in both cAMP and ATP fractions, and basal activity was subtracted to correct for spontaneous activity. Reference compounds used to assess cannabinoid CB$_2$ receptor mediated adenylate cyclase activity were the full cannabinoid CB$_2$ receptor agonists JWH-133 (Huffman, 1999$^b$) and WIN 55,212-2 (Huffman, 1999$^a$), and the inverse agonist or antagonist SR-144528 (Rinaldi-Carmona, 1998). Compounds were studied in a concentration range of $10^{-10}$ M to $10^{-6}$ M. pEC$_{50}$ and the pA$_2$ were calculated according to Cheng-Prusoff equation (Cheng and Prusoff, 1973). Two independent experiments were performed in triplicate.

Example 7

Pharmacological Test Results

Cannabinoid CB$_1$/CB$_2$ receptor affinity data, expressed as pK$_i$ values (mean results of at least three independent experiments, performed according to the protocols given above) as well as CB$_1$ receptor agonist functional data of representative compounds of this invention are shown in the table below.

| | In vitro pharmacology | | |
|---|---|---|---|
| | receptor binding | | functional activity h-$CB_1$ agonistic activity |
| compound | Human $CB_1$ [$^3$H]-CP-55,940 $pK_i$ | Human $CB_2$ [$^3$H]-CP-55,940 $pK_i$ | [$^3$H]-Arachidonic acid $pEC_{50}$ |
| Compound 1 | 8.1 | 8.4 | 8.1 |
| Compound 2 | 7.9 | 8.4 | 7.4 |
| Compound 19 | 7.6 | 8.1 | 7.0 |
| Compound 39 | 7.0 | 7.9 | 7.2 |

Example 8

Pharmaceutical Preparations

For clinical use, compounds of formula (I) are formulated into pharmaceutical compositions that are important and novel embodiments of the invention because they contain the compounds, and, in at least one embodiment, specific compounds disclosed herein. Types of pharmaceutical compositions that may be used include: tablets, chewable tablets, capsules (including microcapsules), solutions, parenteral solutions, ointments (creams and gels), suppositories, suspensions, and other types disclosed herein, or are apparent to a person skilled in the art from the specification and general knowledge in the art. The active ingredient for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (I) in admixture with at least one pharmaceutically acceptable adjuvant, diluent and/or carrier. The total amount of active ingredients suitably is in the range of from about 0.1% (w/w) to about 95% (w/w) of the formulation, suitably from 0.5% to 50% (w/w) and preferably from 1% to 25% (w/w). In some embodiments, the amount of active ingredient is greater than about 95% (w/w) or less than about 0.1% (w/w).

The compounds of the invention can be brought into forms suitable for administration by means of usual processes using pharmaceutically acceptable carriers such as liquid or solid, powdered ingredients, such as the pharmaceutically customary liquid or solid fillers and extenders, solvents, emulsifiers, lubricants, flavorings, colorings and/or buffer substances. Frequently used carriers or auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet is prepared using the ingredients below:

| Ingredient | Quantity (mg/tablet) |
|---|---|
| COMPOUND No. 1 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in the treatment of a condition in which modulation of cannabinoid $CB_1$ receptors is desired, and methods of medical treatment or comprising the administration of a therapeutically effective total amount of at least one compound of formula (I), or, after administration, to a patient suffering from, or susceptible to, a condition in which modulation of cannabinoid CB$_1$ receptors is required or desired.

By way of example and not of limitation, several pharmaceutical compositions are given, comprising preferred active compounds for systemic use or topical application. Other compounds of the invention or combinations thereof, may be used in place of (or in addition to) said compounds. The concentration of the active ingredient may be varied over a wide range as discussed herein. The amounts and types of ingredients that may be included are well known in the art.

BIBLIOGRAPHY

To the extend in which the following references are useful to one skilled in the art, or to more fully describe this invention, they are incorporated herein by reference. Neither these, nor any other documents or quotes cited herein, nor citations to any references, are admitted to be prior art documents or citations.

Adam, J. et al., Progress in Med. Chem. 2006, 44, 207-329; Eds. King and Lawton, Elsevier, Amsterdam
Albericio, F., et al., *Tetrahedron Lett.,* 38, 4853-4856, 1997.
Akaji, K. et al., *Tetrahedron Lett.,* 35, 3315-3318, 1994.
Ashton et al., Neuroscience Lett. 2006, 396, 113-116.
Barluenga et al. Chem. Eur. J., 5, (3) 883-896, 1999
Bickel, M. H., "*The pharmacology and Biochemistry of N-oxides*", Pharmacological Reviews, 21(4), 325-355, 1969.
Bodanszky, M. and A. Bodanszky: *The Practice of Peptide Synthesis*, Springer-Verlag, New York, ISBN: 0-387-57505-7, 1994.
Boyd, S. T. and Fremming, B. A. Ann. Pharmacother. 2005, 39, 684-690
Carai, M. A. M. et al., Life Sc. 2005, 77, 2339-2350
Cheng, Y. and Prusoff, W. H., *Biochem. Pharmacol.,* 22, 3099-3108, 1973
De Petrocellis, L. et al., *Br. J. Pharmacol.,* 141, 765-774, 2004.
Di Marzo, V. et al., *Nature Rev. Drug Discov.,* 3, 771-784, 2004.
Giblin et al., J. Med. Chem. 2007, 50, 2597-2600
Ibrahim et al., PNAS 2005, 102, 3093-3098;
Hertzog, D. L. *Expert Opin. Ther. Patents,* 14, 1435-1452, 2004
Högenauer, E. K. Expert Opin. Ther. Patents 2007, 17, 1457.
Huffman et al., Curr. Med. Chem., 6, 705-720, 1999
Huffman et al., Bioorg. Med. Chem., 7, 2905-2914, 1999 JP 61 189270
Lambert, D. M. and Fowler, C. J. *J. Med. Chem.,* 48, 5059-5087, 2005.
Lange, J. H. M. et al., *J. Med. Chem.,* 47, 627-643, 2004.
Lange, J. H. M. et al., *Bioorg. Med. Chem. Lett,* 15, 4794-4798, 2005.
Lange, J. H. M. and Kruse, C. G., C. *Curr. Opin. Drug Discovery Dev,* 7, 498-506, 2004
Lange, J. H. M. and Kruse, C. G. *Drug Discov. Today,* 10, 693-702, 2005;
Miyaura, N. and Suzuki, A., *Chem. Rev.* 1995, 95, 2457-2483.
Montalbetti, C. A. G. N. & V. Falque, *Tetrahedron,* 61, 10827-52. 2005.
Muccioli, G. G. et al., *Curr. Med. Chem.,* 12, 1361-1394, 2005
Muccioli, G. G. and Lambert, D. M., *Expert Opin. Ther. Patents,* 16, 1405-1423, 2006
Ofek et al., *PNAS* 2006, 103, 696-701.
Ogata, J., et al., J. Med. Chem. 1987, 30, 1054-1068, 1987[a]
Ogata, J., et al., J. Med. Chem. 1987, 30, 1497-1502, 1987[b]
Padgett, L. W. *Life Sc.,* 77, 1767-1798, 2005.

Raitio, K. H., et al., Curr. Med. Chem., 12, 1217-1237, 2005.
Reggio, P. H. Curr. Pharm. Des. 2003, 9, 1607-1633
Rinaldi-Carmona et al., J. Pharmacol. Exp. Ther., 284, 644-650, 1998
Smith, R. A. and Fathi, Z. *IDrugs,* 8, 53-66, 2005.
Sorbera, L. A. et al. Drugs Fut. 2005, 30, 128-137
Thakur, G. A. et al., *Mini-Rev. Med. Chem.,* 5, 631-640, 2005.
Vandevoorde, S, and Lambert, D. M. *Curr. Pharm. Des.,* 11, 2647-68, 2005
Van Sickle, M. D. et al., Science, 310, 329-332, 2005
Wang et al., Synth. Commun., 33 (9), 1449-1457, 2003.
WO 01/070700, WO 03/026647, WO 03/026648, WO 03/079973, WO 2005/074920 and WO 2006/068933

What is claimed is:
1. A compound of formula (I):

or a tautomer, stereoisomer, N-oxide, isotopically-labelled analogue, or pharmacologically acceptable salt of any of the foregoing, wherein:

R is selected from the group consisting of:
$C_{3-10}$ linear alkyl, $C_{4-10}$ branched alkyl, $C_{4-10}$ alkynyl, $C_{3-10}$-heteroalkyl, and $C_{5-8}$-cycloalkyl-$C_{1-5}$-alkyl, optionally substituted with 1-3 fluorine atoms,
aryl-$C_{1-5}$-alkyl and heteroaryl-$C_{1-3}$-alkyl, optionally substituted with 1-3 substituents Y, wherein Y is the same or different, and is selected from the group consisting of methyl, ethyl, methoxy, ethoxy, halogen, trifluoromethyl, trifluoromethoxy and cyano,
cyclopropyl, optionally substituted with $C_{1-5}$-alkyl, benzyl, aryl, and heteroaryl, which are optionally substituted with 1-3 substituents Y, wherein Y is the same or different, and is selected from the group consisting of methyl, ethyl, methoxy, ethoxy, halogen, trifluoromethyl, trifluoromethoxy and cyano;

$R_2$ is selected from the group consisting of aryl and heteroaryl, which are optionally substituted with 1-5 substituents Y, wherein Y is the same or different, and is chosen from methyl, ethyl, methoxy, ethoxy, halogen, trifluoromethyl, trifluoromethoxy and cyano;

n is 0 or 1;

$R_3$ is selected from the group consisting of:
linear and branched $C_{3-10}$ alkyl, $C_{3-8}$ cycloalkyl, $C_{5-10}$ bicloalkyl, $C_{6-10}$ tricycloalkyl and $C_{8-11}$ tetracycloalkyl, which are optionally substituted with 1-5 substituents selected from the group consisting of methyl, ethyl, hydroxy, amino, and fluoro,
$C_{3-8}$ cycloalkyl substituted with aryl and heteroaryl, wherein the aryl and heteroaryl are optionally substituted with 1-5 substituents Y, wherein Y is the same or different, and is selected from the group consisting of methyl, ethyl, methoxy, ethoxy, halogen, trifluoromethyl, trifluoromethoxy and cyano,
$C_{5-8}$ heterocycloalkyl, $O_{6-10}$ bicycloheteroalkyl, and $C_{7-10}$ tricycloheteroalkyl, which are optionally substituted with 1-5 substituents selected from the group consisting of methyl, ethyl, hydroxy, amino, and fluoro, $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, which are optionally substituted with 1-5 substituents selected from the group consisting of methyl, ethyl, hydroxy, amino, and fluoro, branched and linear $C_{3-8}$ heterocycloalkyl-$C_{1-3}$-alkyl, $C_{5-10}$ bicycloheteroalkyl-$C_{1-3}$-alkyl, and $C_{6-10}$ tricycloheteroalkyl-$C_{1-3}$-alkyl, which are optionally substituted with 1-5 substituents selected from the group consisting of methyl, ethyl, hydroxy, amino, and fluoro, aryl and heteroaryl, optionally substituted with 1-5 substituents Y, wherein Y is the same or different, and is selected from the group consisting of methyl, ethyl, methoxy, ethoxy, halogen, trifluoromethyl, trifluoromethoxy and cyano, aryl-$C_{1-5}$-alkyl, heteroaryl-$C_{1-5}$-alkyl and di(hetero)aryl-$C_{1-5}$-alkyl, wherein the phenyl and heteroaromatic rings are optionally substituted with 1-5 substituents Y, wherein Y is the same or different, and is selected from the group consisting of methyl, ethyl, methoxy, ethoxy, halogen, trifluoromethyl, trifluoromethoxy and cyano, linear and branched $C_{4-8}$ alkenyl, and $C_{4-8}$ alkynyl, which are optionally substituted with 1-3 fluorine atoms, with the proviso that when n=1, $R_3$ is selected from the group consisting of branched and linear $C_{2-10}$ heteroalkyl, comprising 1-2 heteroatoms selected from the group consisting of N, O, and S;

$R_5$ is selected from the group consisting of hydrogen and $C_{1-2}$ alkyl, which is optionally substituted with 1-3 fluorine atoms; and $R_6$ is $C_{1-2}$ alkyl, which is optionally substituted with 1-3 fluorine atoms.

2. The compound according to claim 1, wherein $R_2$ is selected from the group consisting of phenyl, thienyl and pyridyl, which are optionally substituted with 1, 2, or 3 substituents Y, wherein Y is the same or different, and is selected from the group consisting of methyl, ethyl, methoxy, ethoxy, halogen, trifluoromethyl, trifluoromethoxy and cyano.

3. The compound according claim 2, wherein n=1.

4. The compound according to claim 3, wherein $R_5$ is selected from the group consisting of hydrogen and methyl, and $R_6$ is methyl.

5. The compound according to claim 4, wherein R is selected from the group consisting of $C_{4-8}$ branched and $C_{3-8}$ linear alkyl, which are optionally substituted with 1-3 fluorine atoms, and $R_2$ is phenyl, which is optionally substituted with 1, 2, or 3 substituents Y, wherein Y is the same or different, and is selected from the group consisting of methyl, ethyl, methoxy, ethoxy, halogen, trifluoromethyl, trifluoromethoxy and cyano.

6. The compound according to claim 5, wherein R is $C_{3-5}$ linear alkyl, and $R_2$ is phenyl, which is optionally substituted with one or more halogen atoms.

7. The compound according to claim 1, wherein the compound is an optically active enantiomer.

8. A medicament comprising a compound of formula (I):

or a tautomer, stereoisomer, N-oxide, isotopically-labelled analogue, or pharmacologically acceptable salt of any of the foregoing, wherein:

R is selected from the group consisting of:
$C_{3-10}$ linear alkyl, $C_{4-10}$ branched alkyl, $C_{4-10}$ alkynyl, $C_{3-10}$-heteroalkyl, and $C_{5-8}$-cycloalkyl-$C_{1-5}$-alkyl, which are optionally substituted with 1-3 fluorine atoms, aryl-$C_{1-3}$-alkyl and heteroaryl-$C_{1-3}$-alkyl, optionally substituted with 1-3 substituents Y, wherein Y is the same or different, and is selected from the group consisting of methyl, ethyl, methoxy, ethoxy, halogen, trifluoromethyl, trifluoromethoxy and cyano, cyclopropyl, optionally substituted with $C_{1-5}$-alkyl, benzyl, aryl, and heteroaryl, which are optionally substituted with 1-3 substituents Y, wherein Y is the same or different, and is selected from the group consisting of methyl, ethyl, methoxy, ethoxy, halogen, trifluoromethyl, trifluoromethoxy and cyano;

$R_2$ is selected from the group consisting of aryl and heteroaryl, which are optionally substituted with 1-5 substituents Y, wherein Y is the same or different, and is selected from the group consisting of methyl, ethyl, methoxy, ethoxy, halogen, trifluoromethyl, trifluoromethoxy and cyano;

n is 0 or 1;

$R_3$ is selected from the group consisting of:
linear and branched $C_{3-10}$ alkyl, $C_{3-8}$ cycloalkyl, $C_{5-10}$ bicycloalkyl, $C_{6-10}$ tricycloalkyl and $C_{8-11}$ tetracycloalkyl, which are optionally substituted with 1-5 substituents selected from the group consisting of methyl, ethyl, hydroxy, amino, and fluoro, $C_{3-8}$ cycloalkyl substituted with aryl and heteroaryl, wherein the aryl and heteroaryl are optionally substituted with 1-5 substituents Y, wherein Y is the same or different, and is selected from the group consisting of methyl, ethyl, methoxy, ethoxy, halogen, trifluoromethyl, trifluoromethoxy and cyano, $C_{5-8}$ heterocycloalkyl, $C_{6-10}$ bicycloheteroalkyl, and $C_{7-10}$ tricycloheteroalkyl, which are optionally substituted with 1-5 substituents selected from the group consisting of methyl, ethyl, hydroxy, amino, and fluoro, $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, which are optionally substituted with 1-5 substituents selected from the group consisting of methyl, ethyl, hydroxy, amino, and fluoro, branched and linear $C_{3-8}$ heterocycloalkyl-$C_{1-3}$-alkyl, $C_{5-10}$ bicycloheteroalkyl-$C_{1-3}$-alkyl, and $C_{6-10}$ tricycloheteroalkyl-$C_{1-3}$-alkyl, which groups optionally substituted with 1-5 substituents selected from the group consisting of methyl, ethyl, hydroxy, amino, and fluoro, aryl and heteroaryl, optionally substituted with 1-5 substituents Y, wherein Y is the same or different, and is selected from the group consisting of methyl, ethyl, methoxy, ethoxy, halogen, trifluoromethyl, trifluoromethoxy and cyano, aryl-$C_{1-5}$-alkyl, heteroaryl-$C_{1-5}$-alkyl and di(hetero)aryl-$C_{1-5}$-alkyl, wherein the phenyl and heteroaromatic rings are optionally substituted with 1-5 substituents Y, wherein Y is the same or different, and is selected from the group consisting of methyl, ethyl, methoxy, ethoxy, halogen, trifluoromethyl, trifluoromethoxy and cyano, linear and branched $C_{4-8}$ alkenyl, and $C_{4-8}$ alkynyl, which are optionally substituted with 1-3 fluorine atoms, with the proviso that when n=1, $R_3$ is selected from the group consisting of branched and linear $C_{2-10}$ heteroalkyl, comprising 1-2 heteroatoms selected from the group consisting of N, O, and S;

$R_5$ is selected from the group consisting of hydrogen and $C_{1-2}$ alkyl, which is optionally substituted with 1-3 fluorine atoms; and $R_6$ is $C_{1-2}$ alkyl, which is optionally substituted with 1-3 fluorine atoms.

9. A method of treating at least one condition selected from the group consisting of multiple sclerosis, traumatic brain injury, pain, appetite disorders, epilepsy, Alzheimer's disease, Tourette's syndrome, cerebral ischaemia, osteoporosis, emesis, and nausea, the method comprising administering to a mammal in need thereof a therapeutically effective amount of a compound of formula (I):

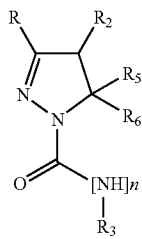

(I)

or a tautomer, stereoisomer, N-oxide, isotopically-labelled analogue, or pharmacologically acceptable salt of any of the foregoing, wherein:

R is selected from the group consisting of:

$C_{3-10}$ linear alkyl, $C_{4-10}$ branched alkyl, $C_{4-10}$ alkynyl, $C_{3-10}$-heteroalkyl, and $C_{5-8}$-cycloalkyl-$C_{1-5}$-alkyl, which are optionally substituted with 1-3 fluorine atoms, aryl-$C_{1-3}$-alkyl and heteroaryl-$C_{1-3}$-alkyl, optionally substituted with 1-3 substituents Y, wherein Y is the same or different, and is selected from the group consisting of methyl, ethyl, methoxy, ethoxy, halogen, trifluoromethyl, trifluoromethoxy and cyano, cyclopropyl, optionally substituted with $C_{1-5}$-alkyl, benzyl, aryl, and heteroaryl, which are optionally substituted with 1-3 substituents Y, wherein Y is the same or different, and is selected from the group consisting of methyl, ethyl, methoxy, ethoxy, halogen, trifluoromethyl, trifluoromethoxy and cyano;

$R_2$ is selected from the group consisting of aryl and heteroaryl, which are optionally substituted with 1-5 substituents Y, wherein Y is the same or different, and is selected from the group consisting of methyl, ethyl, methoxy, ethoxy, halogen, trifluoromethyl, trifluoromethoxy and cyano;

n is 0 or 1;

$R_3$ is selected from the group consisting of:

linear and branched $C_{3-10}$ alkyl, $C_{3-8}$ cycloalkyl, $C_{5-10}$ bicycloalkyl, $C_{6-10}$ tricycloalkyl and $C_{8-11}$ tetracycloalkyl, which are optionally substituted with 1-5 substituents selected from the group consisting of methyl, ethyl, hydroxy, amino, and fluoro, $C_{3-8}$ cycloalkyl substituted with aryl and heteroaryl, wherein the aryl and heteroaryl are optionally substituted with 1-5 substituents Y, wherein Y is the same or different, and is selected from the group consisting of methyl, ethyl, methoxy, ethoxy, halogen, trifluoromethyl, trifluoromethoxy and cyano, $C_{5-8}$ heterocycloalkyl, $C_{6-10}$ bicycloheteroalkyl, and $C_{7-10}$ tricycloheteroalkyl, which are optionally substituted with 1-5 substituents selected from the group consisting of methyl, ethyl, hydroxy, amino, and fluoro, $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, which are optionally substituted with 1-5 substituents selected from the group consisting of methyl, ethyl, hydroxy, amino, and fluoro, branched and linear $C_{3-8}$ heterocycloalkyl-$C_{1-3}$-alkyl, $C_{5-10}$ bicycloheteroalkyl-$C_{1-3}$-alkyl, and $C_{6-10}$ tricycloheteroalkyl-$C_{1-3}$-alkyl, which groups optionally substituted with 1-5 substituents selected from the group consisting of methyl, ethyl, hydroxy, amino, and fluoro, aryl and heteroaryl, optionally substituted with 1-5 substituents Y, wherein Y is the same or different, and is selected from the group consisting of methyl, ethyl, methoxy, ethoxy, halogen, trifluoromethyl, trifluoromethoxy and cyano, aryl-$C_{1-5}$-alkyl, heteroaryl-$C_{1-5}$-alkyl and di(hetero)aryl-$C_{1-5}$-alkyl, wherein the phenyl and heteroaromatic rings are optionally substituted with 1-5 substituents Y, wherein Y is the same or different, and is selected from the group consisting of methyl, ethyl, methoxy, ethoxy, halogen, trifluoromethyl, trifluoromethoxy and cyano, linear and branched $C_{4-8}$ alkenyl, and $C_{4-8}$ alkynyl, which are optionally substituted with 1-3 fluorine atoms, with the proviso that when n=1, $R_3$ is selected from the group consisting of branched and linear $C_{2-10}$ heteroalkyl, comprising 1-2 heteroatoms selected from the group consisting of N, O, and S;

$R_5$ is selected from the group consisting of hydrogen and $C_{1-2}$ alkyl, which is optionally substituted with 1-3 fluorine atoms; and $R_6$ is $C_{1-2}$ alkyl, which is optionally substituted with 1-3 fluorine atoms.

10. A pharmaceutical composition comprising, at least one pharmaceutically acceptable carrier, and a therapeutically effective amount of at least one compound of formula (I):

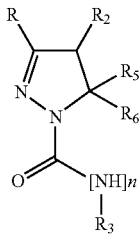

or a tautomer, stereoisomer, N-oxide, isotopically-labelled analogue, or pharmacologically acceptable salt of any of the foregoing, wherein:

R is selected from the group consisting of:
- $C_{3-10}$ linear alkyl, $C_{4-10}$ branched alkyl, $C_{4-10}$ alkynyl, $C_{3-10}$-heteroalkyl, and $C_{5-8}$-cycloalkyl-$C_{1-5}$-alkyl, which are optionally substituted with 1-3 fluorine atoms,
- aryl-$C_{1-3}$-alkyl and heteroaryl-$C_{1-3}$-alkyl, optionally substituted with 1-3 substituents Y, wherein Y is the same or different, and is selected from the group consisting of methyl, ethyl, methoxy, ethoxy, halogen, trifluoromethyl, trifluoromethoxy and cyano,
- cyclopropyl, optionally substituted with $C_{1-5}$-alkyl, benzyl, aryl, and heteroaryl, which are optionally substituted with 1-3 substituents Y, wherein Y is the same or different, and is selected from the group consisting of methyl, ethyl, methoxy, ethoxy, halogen, trifluoromethyl, trifluoromethoxy and cyano;

$R_2$ is selected from the group consisting of aryl and heteroaryl, which are optionally substituted with 1-5 substituents Y, wherein Y is the same or different, and is selected from the group consisting of methyl, ethyl, methoxy, ethoxy, halogen, trifluoromethyl, trifluoromethoxy and cyano;

n is 0 or 1;

$R_3$ is selected from the group consisting of:
- linear and branched $C_{3-10}$ alkyl, $C_{3-8}$ cycloalkyl, $C_{5-10}$ bicycloalkyl, $C_{6-10}$ tricycloalkyl and $C_{8-11}$ tetracycloalkyl, which are optionally substituted with 1-5 substituents selected from the group consisting of methyl, ethyl, hydroxy, amino, and fluoro,
- $C_{3-8}$ cycloalkyl substituted with aryl and heteroaryl, wherein the aryl and heteroaryl are optionally substituted with 1-5 substituents Y, wherein Y is the same or different, and is selected from the group consisting of methyl, ethyl, methoxy, ethoxy, halogen, trifluoromethyl, trifluoromethoxy and cyano,
- $C_{5-8}$ heterocycloalkyl, $C_{6-10}$ bicycloheteroalkyl, and $C_{7-10}$ tricycloheteroalkyl, which are optionally substituted with 1-5 substituents selected from the group consisting of methyl, ethyl, hydroxy, amino, and fluoro,
- $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, which are optionally substituted with 1-5 substituents selected from the group consisting of methyl, ethyl, hydroxy, amino, and fluoro,
- branched and linear $C_{3-8}$ heterocycloalkyl-$C_{1-3}$-alkyl, $C_{6-10}$ bicycloheteroalkyl-$C_{1-3}$-alkyl, and $C_{6-10}$ tricycloheteroalkyl-$C_{1-3}$-alkyl, which groups optionally substituted with 1-5 substituents selected from the group consisting of methyl, ethyl, hydroxy, amino, and fluoro,
- aryl and heteroaryl, optionally substituted with 1-5 substituents Y, wherein Y is the same or different, and is selected from the group consisting of methyl, ethyl, methoxy, ethoxy, halogen, trifluoromethyl, trifluoromethoxy and cyano,
- aryl-$C_{1-5}$-alkyl, heteroaryl-$C_{1-5}$-alkyl and di(hetero)aryl-$C_{1-5}$-alkyl, wherein the phenyl and heteroaromatic rings are optionally substituted with 1-5 substituents Y, wherein Y is the same or different, and is selected from the group consisting of methyl, ethyl, methoxy, ethoxy, halogen, trifluoromethyl, trifluoromethoxy and cyano,
- linear and branched $C_{4-8}$ alkenyl, and $C_{4-8}$ alkynyl, which are optionally substituted with 1-3 fluorine atoms, with the proviso that when n=1, $R_3$ is selected from the group consisting of branched and linear $C_{2-10}$ heteroalkyl, comprising 1-2 heteroatoms selected from the group consisting of N, O, and S;

$R_5$ is selected from the group consisting of hydrogen and $C_{1-2}$ alkyl, which is optionally substituted with 1-3 fluorine atoms; and $R_6$ is $C_{1-2}$ alkyl, which is optionally substituted with 1-3 fluorine atoms.

11. The pharmaceutical composition according to claim 10, further comprising: at least one additional therapeutic agent.

12. A method of treating at least one condition selected from the group consisting of multiple sclerosis, traumatic brain injury, pain, appetite disorders, epilepsy, Alzheimer's disease, Tourette's syndrome, cerebral ischaemia, osteoporosis, emesis, abd nausea, the method comprising administering a pharmaceutical composition to a mammal in need thereof, wherein the pharmaceutical composition comprises at least one pharmaceutically acceptable carrier, and a therapeutically effective amount of at least one compound of formula (I):

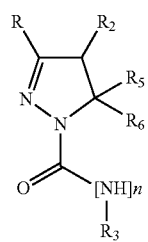

or a tautomer, stereoisomer, N-oxide, isotopically-labelled analogue, or pharmacologically acceptable salt of any of the foregoing, wherein:

R is selected from the group consisting of:
- $C_{3-10}$ linear alkyl, $C_{4-10}$ branched alkyl, $C_{4-10}$ alkynyl, $C_{3-10}$-heteroalkyl, and $C_{5-8}$-cycloalkyl-$C_{1-5}$-alkyl, which are optionally substituted with 1-3 fluorine atoms,
- aryl-$C_{1-3}$-alkyl and heteroaryl-$C_{1-3}$-alkyl, optionally substituted with 1-3 substituents Y, wherein Y is the same or different, and is selected from the group consisting of methyl, ethyl, methoxy, ethoxy, halogen, trifluoromethyl, trifluoromethoxy and cyano,
- cyclopropyl, optionally substituted with $C_{1-5}$-alkyl, benzyl, aryl, and heteroaryl, which are optionally substituted with 1-3 substituents Y, wherein Y is the same or different, and is selected from the group consisting of methyl, ethyl, methoxy, ethoxy, halogen, trifluoromethyl, trifluoromethoxy and cyano;

$R_2$ is selected from the group consisting of aryl and heteroaryl, which are optionally substituted with 1-5 substituents Y, wherein Y is the same or different, and is selected from the group consisting of methyl, ethyl, methoxy, ethoxy, halogen, trifluoromethyl, trifluoromethoxy and cyano;

n is 0 or 1;

$R_3$ is selected from the group consisting of:
- linear and branched $C_{3-10}$ alkyl, $C_{3-8}$ cycloalkyl, $C_{5-10}$ bicycloalkyl, $C_{6-10}$ tricycloalkyl and $C_{8-11}$ tetracycloalkyl, which are optionally substituted with 1-5 substituents selected from the group consisting of methyl, ethyl, hydroxy, amino, and fluoro,
- $C_{3-8}$ cycloalkyl substituted with aryl and heteroaryl, wherein the aryl and heteroaryl are optionally substituted with 1-5 substituents Y, wherein Y is the same or different, and is selected from the group consisting of methyl, ethyl, methoxy, ethoxy, halogen, trifluoromethyl, trifluoromethoxy and cyano,
- $C_{5-8}$ heterocycloalkyl, $C_{6-10}$ bicycloheteroalkyl, and $C_{7-10}$ tricycloheteroalkyl, which are optionally substituted with 1-5 substituents selected from the group consisting of methyl, ethyl, hydroxy, amino, and fluoro,
- $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, which are optionally substituted with 1-5 substituents selected from the group consisting of methyl, ethyl, hydroxy, amino, and fluoro,
- branched and linear $C_{3-8}$ heterocycloalkyl-$C_{1-3}$-alkyl, $C_{5-10}$ bicycloheteroalkyl-$C_{1-3}$-alkyl, and $C_{6-10}$ tricycloheteroalkyl-$C_{1-3}$-alkyl, which groups optionally substituted with 1-5 substituents selected from the group consisting of methyl, ethyl, hydroxy, amino, and fluoro,
- aryl and heteroaryl, optionally substituted with 1-5 substituents Y, wherein Y is the same or different, and is selected from the group consisting of methyl, ethyl, methoxy, ethoxy, halogen, trifluoromethyl, trifluoromethoxy and cyano,
- aryl-$C_{1-5}$-alkyl, heteroaryl-$C_{1-5}$-alkyl and di(hetero)aryl-$C_{1-5}$-alkyl, wherein the phenyl and heteroaromatic rings are optionally substituted with 1-5 substituents Y, wherein Y is the same or different, and is selected from the group consisting of methyl, ethyl, methoxy, ethoxy, halogen, trifluoromethyl, trifluoromethoxy and cyano,
- linear and branched $C_{4-8}$ alkenyl, and $C_{4-8}$ alkynyl, which are optionally substituted with 1-3 fluorine atoms, with the proviso that when n=1, $R_3$ is selected from the group consisting of branched and linear $C_{2-10}$ heteroalkyl, comprising 1-2 heteroatoms selected from the group consisting of N, O, and S;

$R_5$ is selected from the group consisting of hydrogen and $C_{1-2}$ alkyl, which is optionally substituted with 1-3 fluorine atoms; and $R_6$ is $C_{1-2}$ alkyl, which is optionally substituted with 1-3 fluorine atoms.

13. The method according to claim 12, further comprising administering at least one additional therapeutic agent.

14. The method according to claim 12, wherein pain is selected from the group consisting of chronic pain, neuropathic pain, acute pain and inflammatory pain.

* * * * *